United States Patent
Sakurai et al.

(10) Patent No.: US 10,899,110 B2
(45) Date of Patent: *Jan. 26, 2021

(54) OUTER BAG FOR DISPOSABLE BODY WARMER PACKAGING AND DISPOSABLE BODY WARMER

(71) Applicant: KOBAYASHI PHARMACEUTICAL CO., LTD., Osaka (JP)

(72) Inventors: Yuki Sakurai, Osaka (JP); Tsuyoshi Igaue, Osaka (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 108 days.

This patent is subject to a terminal disclaimer.

(21) Appl. No.: 16/064,688

(22) PCT Filed: Dec. 25, 2015

(86) PCT No.: PCT/JP2015/086269
§ 371 (c)(1),
(2) Date: Jun. 21, 2018

(87) PCT Pub. No.: WO2017/109945
PCT Pub. Date: Jun. 29, 2017

(65) Prior Publication Data
US 2019/0001627 A1  Jan. 3, 2019

(51) Int. Cl.
*B32B 15/09* (2006.01)
*B32B 27/30* (2006.01)
(Continued)

(52) U.S. Cl.
CPC .............. *B32B 15/09* (2013.01); *A61F 7/03* (2013.01); *A61F 7/034* (2013.01); *B32B 7/12* (2013.01);
(Continued)

(58) Field of Classification Search
CPC ..... B32B 15/09; B32B 15/20; B32B 2250/05; B32B 2307/31; B32B 2307/4023;
(Continued)

(56) References Cited

U.S. PATENT DOCUMENTS 10,322,860 B2 * 6/2019 Sakurai ................. A61F 7/03
2007/0256677 A1 11/2007 Yim et al.
(Continued)

FOREIGN PATENT DOCUMENTS

CN 104717943 A 6/2015
JP 1-117320 U 8/1989
(Continued)

OTHER PUBLICATIONS

International Search Report (PCT/ISA/210) issued in PCT/JP2015/086264, dated Feb. 23, 2016.
(Continued)

*Primary Examiner* — Yan Lan
(74) *Attorney, Agent, or Firm* — Birch, Stewart, Kolasch & Birch, LLP

(57) ABSTRACT

An outer bag for disposable body warmer packaging and a disposable body warmer are provided that are excellent in a gas barrier property that inhibits permeation of oxygen gas, water vapor and the like, which can allow swelling due to hydrogen gas generated during a storage period to be prevented.

Provided is an outer bag for disposable body warmer packaging having an accommodating portion accommodating a disposable body warmer accommodated in an air-permeable inner bag and generating heat through contact with air, the outer bag comprising a low air-permeability portion having an oxygen permeability of 1.5 to 20 cc/m$^2$·day·atm measured at 20° C. and 90% RH and a water vapor permeability of 0.05 to 10 g/m$^2$·day measured at 40° C. and 90% RH; and
(Continued)

an air-impermeable portion having an oxygen permeability of 1.3 cc/m²·day·atm or lower measured at 20° C. and 90% RH and a water vapor permeability of 2.0 g/m²·day or lower measured at 40° C. and 90% RH, wherein the outer bag for disposable body warmer packaging has at least one heat-sealed portion formed by heat-sealing one or more laminated sheets, and the low air-permeability portion is provided in at least a part of a region adjacent to the heat-sealed portion.

9 Claims, 20 Drawing Sheets

(51) Int. Cl.

| | | |
|---|---|---|
| *B32B 27/32* | (2006.01) | |
| *B32B 27/36* | (2006.01) | |
| *B32B 7/12* | (2006.01) | |
| *A61F 7/03* | (2006.01) | |
| *B32B 15/20* | (2006.01) | |
| *A61F 7/02* | (2006.01) | |

(52) U.S. Cl.
CPC ............ *B32B 15/20* (2013.01); *B32B 27/304* (2013.01); *B32B 27/32* (2013.01); *B32B 27/36* (2013.01); *A61F 2007/0257* (2013.01); *A61F 2007/0258* (2013.01); *A61F 2007/038* (2013.01); *B32B 2250/05* (2013.01); *B32B 2307/31* (2013.01); *B32B 2307/4023* (2013.01); *B32B 2307/518* (2013.01); *B32B 2307/7244* (2013.01); *B32B 2307/7246* (2013.01); *B32B 2439/46* (2013.01)

(58) Field of Classification Search
CPC ...... B32B 2307/518; B32B 2307/7244; B32B 2307/7246; B32B 2439/46; B32B 27/304; B32B 27/32; B32B 27/36; B32B 7/12; A61F 2007/0257; A61F 2007/0258; A61F 2007/038; A61F 7/03; A61F 7/034

See application file for complete search history.

(56) References Cited

U.S. PATENT DOCUMENTS

| | | |
|---|---|---|
| 2016/0242960 A1 | 8/2016 | Igaue |
| 2019/0009960 A1 | 1/2019 | Sakurai et al. |

FOREIGN PATENT DOCUMENTS

| | | | |
|---|---|---|---|
| JP | 3-286759 | A | 12/1991 |
| JP | 4-48182 | U | 4/1992 |
| JP | 11-239584 | A | 9/1999 |
| JP | 2003-231221 | A | 8/2003 |
| JP | 3107759 | U | 2/2005 |
| JP | 2006-347582 | A | 12/2006 |
| WO | WO 2015/045185 | A1 | 4/2015 |
| WO | WO 2017/109944 | A1 | 6/2017 |

OTHER PUBLICATIONS

International Search Report (PCT/ISA/210) issued in PCT/JP2015/086269, dated Feb. 23, 2016.
Written Opinion of the International Searching Authority (PCT/ISA/237) issued in PCT/JP2015/086269, dated Feb. 23, 2016.
Extended European Search Report, dated Jul. 19, 2019, for European Application No. 15911381.0.
Extended European Search Report, dated Jul. 19, 2019, for European Application No. 15911382.8.

\* cited by examiner (a)

(b)

(a)

(b)

(a)                    (b)

(a)

(b)

(a)

(b)

(a)

(b)

(a)

(b)

(a)  (b)

000
OUTER BAG FOR DISPOSABLE BODY WARMER PACKAGING AND DISPOSABLE BODY WARMER

TECHNICAL FIELD

The present invention relates to an outer bag for disposable body warmer packaging, and a disposable body warmer.

BACKGROUND ART

A disposable body warmer is a body warmer that utilizes heat generation caused by the oxidation action of iron powders. In the disposable body warmer, usually, an inner bag including an air-permeable bag of a non-woven fabric, paper, or the like which accommodates an exothermic composition containing iron powders as an exothermic element, a salt as an oxidation catalyst, activated carbon for intake of oxygen, water for oxidizing iron, a water-retaining agent for retaining the water, and the like, is accommodated and airtightly packaged in an outer bag made of an air-impermeable film cutting off contact with air in an unused state.

An outer bag for disposable body warmer packaging is required to be excellent in gas barrier property for inhibiting permeation of air, in particular, oxygen gas, water vapor, and the like. If the outer bag for disposable body warmer packaging is poor in its gas barrier property against oxygen gas and water vapor, any gas and water vapor in the outer bag for disposable body warmer packaging will escape outside during storage for a long period, producing a depressurized (vacuum) state and consequently causing the outer bag to be depressed, which is not preferable in terms of appearance. In addition, when such an outer bag in a depressurized (vacuum) state is stored for a long period and thereafter used as a disposable body warmer, the duration of heat generation thereof is often short. As an air-impermeable film forming the outer bag for disposable body warmer packaging, a multilayer film is generally used in which a gas barrier layer is provided on a sealant layer and a heat-resistant resin layer is provided on an outermost layer. Two of such air-impermeable multilayer films are stacked each other and the peripheries of the sealant layers located inward are heat-sealed to each other into the form of a bag. The outer bag for disposable body warmer packaging is thus manufactured.

Meanwhile, it is known that a trace amount of hydrogen gas is generated when a disposable body warmer is stored in an unused state for a long period. The outer bag for disposable body warmer packaging becomes swollen due to the hydrogen gas, and this is not preferable in terms of appearance. In addition, the outer bag is broken when the swelling reaches its limit, and an exothermic composition accommodated in an inner bag is oxidized to generate heat, thereby causing the function as a disposable body warmer to be impaired. For this reason, hydrogen gas permeability is required to such an extent that the outer bag for disposable body warmer packaging is not swollen during the long storage period. However, as described above, it is also required that the outer bag for disposable body warmer packaging excel in the gas barrier property for inhibiting permeation of oxygen gas, water vapor, and the like. As a result, when the bas barrier property of the air-impermeable film forming the outer bag for disposable body warmer packaging is made higher, the hydrogen gas permeability is decreased, causing swelling during the long storage period.

As an outer bag for disposable body warmer packaging that takes the hydrogen gas permeability into consideration, an outer bag for disposable body warmer packaging has been proposed which includes a plastic film and a vapor-deposited layer obtained by vapor deposition of metal such as aluminum on the plastic film, where film exposure portions without any vapor-deposited layer are scattered provided on the surface of the plastic film, the total area of the exposure portions falls within the range of $1/1000$ to $1/10$ to the surface area of the outer bag (PTL 1). In PTL 1, storage experimentation where three-month storage at a temperature of 40° C. is performed is specifically illustrated. Although this condition indicates that the experimentation illustrated therein is equivalent to 1.5-year storage experimentation at room temperature, it cannot be said to be sufficient in terms of temperature or time. Thus, an actual outer bag for disposable body warmer packaging which can withstand severer storage conditions may be required.

As described above, although various outer bags for disposable body warmer packaging have been proposed, they still leave room for improvement and an outer bag for disposable body warmer packaging and disposable body warmer are required which can ensure an optimum gas permeation property and gas barrier property as a product over a long period.

CITATION LIST

Patent Literature

PTL 1: Japanese Utility Model Laid-Open No. H04-048182

SUMMARY OF INVENTION

Technical Problem

In view of the above, an object of the present invention is to provide an outer bag for disposable body warmer packaging and disposable body warmer that are excellent in a gas barrier property that selectively inhibits permeation of oxygen gas, water vapor and the like, which can allow swelling due to hydrogen gas generated during a storage period to be prevented.

Solution to Problem

The present inventors have made intensive studies in order to solve the above problem, and as a result, have found that, when an outer bag for disposable body warmer packaging is swollen by hydrogen gas and the outer bag is broken, the pressure due to the swelling concentrates at the heat-sealed portion and the breakage begins at the heat-sealed portion, and realized that the breakage can be prevented by controlling the hydrogen gas permeability in the region adjacent to the heat-sealed portion of the outer bag. Specifically, the inventors realized that an outer bag for disposable body warmer packaging having an accommodating portion accommodating a disposable body warmer accommodated in an air-permeable inner bag and generating heat through contact with air, the outer bag including a low air-permeability portion having an oxygen permeability of 1.5 to 20 cc/m²·day·atm measured at 20° C. and 90% RH and a water vapor permeability of 0.05 to 10 g/m²·day measured at 40° C. and 90% RH; and an air-impermeable portion having an oxygen permeability of 1.3 cc/m²·day·atm or lower measured at 20° C. and 90% RH and a water vapor permeability of 2.0 g/m²·day or lower measured at 40° C. and 90% RH, the outer bag for disposable body warmer packaging having at least one heat-sealed portion formed by heat-sealing one or more laminated sheets, the low air-permeability portion being provided in at least a part of a region adjacent to the heat-sealed portion, can achieve optimum oxygen gas permeability, water vapor permeation property, and hydrogen gas permeability without impairing the seal strength, impact resistance, and weatherability, and this knowledge has led to completion of the present invention. The specific implementations of the body warmer of the present invention are as follows:

[1] An outer bag for disposable body warmer packaging having an accommodating portion accommodating a disposable body warmer accommodated in an air-permeable inner bag, wherein the outer bag comprising a low air-permeability portion having an oxygen permeability of 1.5 to 20 cc/m²·day·atm measured at 20° C. and 90% RH and a water vapor permeability of 0.05 to 10 g/m²·day measured at 40° C. and 90% RH; and an air-impermeable portion having an oxygen permeability of 1.3 cc/m²·day·atm or lower measured at 20° C. and 90% RH and a water vapor permeability of 2.0 g/m²·day or lower measured at 40° C. and 90% RH; and wherein the outer bag for disposable body warmer packaging having at least one heat-sealed portion formed by heat-sealing one or more laminated sheets, and the low air-permeability portion is provided in at least a part of a region adjacent to the heat-sealed portion.

[2] The outer bag for disposable body warmer packaging according to [1], wherein a ratio of area of the low air-permeability portion to a total internal area of the accommodating portion is 1 to 50%.

[3] The outer bag for disposable body warmer packaging according to [1] or [2], wherein a low air-permeability layer and an air-impermeable layer are provided on one sealant layer, and the low air-permeability portion has the low air-permeability layer, and the air-impermeable portion has the low air-permeability layer and the air-impermeable layer.

[4] The outer bag for disposable body warmer packaging according to [1] or [2], wherein a low air-permeability layer and an air-impermeable layer are provided on one sealant layer, and the low air-permeability portion has the low air-permeability layer, and the air-impermeable portion has the air-impermeable layer.

[5] The outer bag for disposable body warmer packaging according to [1] or [2], wherein the low air-permeability portion has a first substrate and a low air-permeability layer laminated on the first substrate, and the air-impermeable portion has a second substrate and an air-impermeable layer laminated on the second substrate, and the first substrate and the second substrate are heat-sealed.

[6] The outer bag for disposable body warmer packaging according to any one of [3] to [5], wherein the low air-permeability layer comprises a homopolymer or copolymer of vinylidene chloride, and the air-impermeable layer comprises a metal or metal oxide.

[7] A disposable body warmer packaged by the outer bag according to any one of [1] to [6].

Advantageous Effects of Invention

The outer bag for disposable body warmer packaging of the present invention has an optimum gas barrier property without impairing seal strength, impact resistance, and weatherability as an outer bag for disposable body warmer packaging that blocks permeation of oxygen gas and water vapors and allows permeation of hydrogen gas.

The disposable body warmer of the present invention is capable of preventing swelling caused by hydrogen gas generated while it is stored and degradation of the exothermic composition due to permeation of oxygen gas and water vapors, so that the body warmer can be stored for a long period without impairing the functionality as a disposable body warmer.

DESCRIPTION OF EMBODIMENTS

Figure 1A:
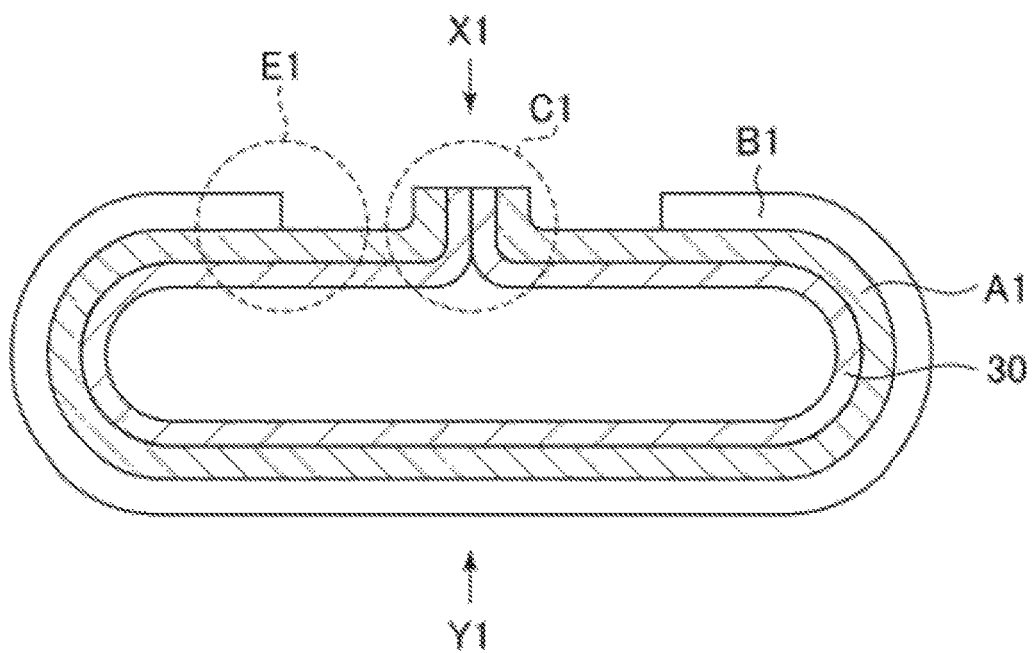
FIG. 1A is a cross-sectional view of an outer bag for disposable body warmer packaging in Embodiment 1 of the present invention.

The outer bag for disposable body warmer packaging and the disposable body warmer of the present invention will be described below with reference to the drawings.

The present invention provides an outer bag for disposable body warmer packaging having an accommodating portion that accommodates a disposable body warmer accommodated in an air-permeable inner bag, wherein the outer bag comprising a low air-permeability portion having an oxygen permeability of 1.5 to 20 cc/m²·day·atm measured at 20° C. and 90% RH and a water vapor permeability of 0.05 to 10 g/m²·day measured at 40° C. and 90% RH; and an air-impermeable portion having an oxygen permeability of 1.3 cc/m²·day·atm or lower measured at 20° C. and 90% RH and a water vapor permeability of 2.0 g/m²·day or lower measured at 40° C. and 90% RH, and wherein the outer bag for disposable body warmer packaging having at least one heat-sealed portion formed by heat-sealing one or more laminated sheets, the low air-permeability portion being provided in at least a part of a region adjacent to the heat-sealed portion.

The oxygen permeability of the low air-permeability portion (at 20° C. and 90% RH) is 1.5 to 20 cc/(m²·day·atm), preferably 2.0 to 15 cc/(m²·day·atm), and more preferably 2.0 to 10 cc/(m²·day·atm). Also, the water vapor permeability in the low air-permeability portion (at 40° C. and 90% RH) is 0.05 to 10 g/(m²·day), and preferably 1.0 to 5.0 g/(m²·day).

The oxygen permeability of the air-impermeable portion (at 20° C. and 90% RH) is 1.3 cc/(m²·day·atm) or lower, preferably 0.01 to 1.3 cc/(m²·day·atm), more preferably 0.01 to 1.15 cc/(m²·day·atm), and most preferably 0.01 to 1.0 cc/(m²·day·atm). Also, the water vapor permeability in the air-impermeable portion (at 40° C. and 90% RH) is 2.0 g/(m²·day) or lower, preferably 0.01 to 2.0 g/(m²·day), and more preferably 0.01 to 1.5 g/(m²·day).

The outer bag for disposable body warmer packaging of the present invention can satisfy the conflicting requirements of allowing hydrogen gas generated inside of the bag to escape to an outside of the bag and preventing intrusion of oxygen gas and water vapor from the outside into the inside of the bag by virtue of the low air-permeability portion provided in at least a part of the region adjacent to the heat-sealed portion.

The region adjacent to the heat-sealed portion in the outer bag for disposable body warmer packaging of the present invention refers to a portion that is in contact with the heat-sealed portion. In the outer bag for disposable body warmer packaging of the present invention, the width of the region adjacent to the heat-sealed portion starting from a point in contact with the heat-sealed portion is preferably 0.1 to 100 mm, more preferably 0.5 to 50 mm, and most preferably 1.0 to 30 mm. Also, in the outer bag for disposable body warmer packaging of the present invention, the ratio of the area of the low air-permeability portion existing in the region adjacent to the heat-sealed portion to the area of the entire low air-permeability portion existing in the outer bag for disposable body warmer packaging is preferably 1 to 50%, more preferably 3 to 50%, and most preferably 5 to 50%.

In the outer bag for disposable body warmer packaging of the present invention, the oxygen permeability and the water vapor permeability of the low air-permeability portion and the air-impermeable portion are defined within the above-identified numerical ranges, and the at least one heat-sealed portion and the low air-permeability portion in at least a part of a region adjacent thereto are provided. Thereby, it is made possible to achieve the effects that it is excellent in its gas barrier property that inhibits permeation of oxygen gas, water vapor and the like, which can allow swelling due to hydrogen gas generated during a storage period to be prevented. For stable and long-term storage of the disposable body warmer, it is required that the oxygen permeability and the water vapor permeability of the low air-permeability portion and the air-impermeable portion be defined within the above-identified numerical ranges and that the low air-permeability portion be provided in at least a part of the region adjacent to the heat-sealed portion. If either of which fails to be satisfied, the desired effects will not be obtained.

In general, an outer bag for disposable body warmer packaging is formed in the form of a bag through publicly known heat-sealing of various types such as stacking a plurality of laminated sheets each made of multiple layers including a sealant layer and subjecting them to four-side sealing; winding a laminated sheet and subjecting it to three-side sealing or three-side pillow, and the like. The present invention is preferably an outer bag for disposable body warmer packaging which includes a low air-permeability layer and an air-impermeable layer as the layers to be laminated on a sealant layer, and is formed such that the low air-permeability portion and the air-impermeable portion will have predetermined ratios through controlling the modes of lamination of the low air-permeability layer and the air-impermeable layer.

In the outer bag for disposable body warmer packaging of the present invention, the ratio of the area of the low air-permeability portion to an internal area of the accommodating portion is preferably 1 to 50%, more preferably 3 to 50%, and much preferably 5 to 50%, and 50% will be preferable as a ratio of area that allows for production by a simplified scheme. The ratio of the area of the air-impermeable portion to the inner area of the accommodating portion is preferably 50 to 99%, more preferably 50 to 97%, and further preferably 50 to 95%, and 50% will be preferable as a ratio of area that allows for production by a simplified scheme. The sum of the low air-permeability portion and the air-impermeable portion is 100%.

In accordance with the outer bag for disposable body warmer packaging of the present invention, the low air-permeability layer and the air-impermeable layer may be provided on one sealant layer. The low air-permeability portion may have the low air-permeability layer. The air-impermeable portion may have the low layer and the air-impermeable layer.

Also, in accordance with the outer bag for disposable body warmer packaging of the present invention, the low air-permeability layer and the air-impermeable layer may be provided on one sealant layer. The low air-permeability portion may have the low air-permeability layer. The air-impermeable portion may have the air-impermeable layer.

Further, in accordance with the outer bag for disposable body warmer packaging of the present invention, the low air-permeability portion may have a first substrate and a low air-permeability layer laminated on the first substrate. The air-impermeable portion may have a second substrate and an air-impermeable layer laminated on the second substrate. The first substrate and the second substrate may be heat-sealed.

It is preferable that the first and second substrates are heat-resistant substrates. Specifically, for example, any film of various resins may be used such as a polyolefin-based resin such as a polyethylene-based resin and a polypropylene-based resin, a cyclic polyolefin-based resin, a polystyrene-based resin, an acrylonitrile-styrene copolymer (AS resin), an acrylonitrile-butadiene-styrene copolymer (ABS resin), a poly(meth)acrylic-based resin, a polycarbonate-based resin, a polyester-based resin such as polyethylene terephthalate and polyethylene naphthalate, a polyamide-based resin such as various nylons, a polyurethane-based resin, an acetal-based resin, and a cellulose-based resin. Among them, a film of a polyester-based resin, a polyolefin-based resin or a polyamide-based resin is preferable, and in particular, a film of biaxially oriented polypropylene, biaxially oriented polyethylene terephthalate or a biaxially oriented polyamide resin is preferable. Various resin films can be produced by a method where one or more of the above various resins are used and such resins are subjected singly or in combinations of two or more to multilayer co-extrusion film formation with an extrusion method, a cast molding method, a T-die method, a cutting method, an inflation method, or other film formation methods. Furthermore, various resin films can be produced by a method where two or more of the resins are used, mixed, and subjected to film formation, or the like. Further, the various resin films can be formed to be uniaxially or biaxially oriented by utilizing, for example, a tentering method or a tubular method. The thicknesses of the first and second substrates are preferably 3 to 500 µm, more preferably 5 to 300 µm, further preferably 10 to 100 µm, and most preferably 15 to 50 µm. The types of the various resins used in and/or thicknesses of the first and second substrates may be the same or different.

The low air-permeability layer is a layer which allows permeation of oxygen gas, water vapor, and hydrogen gas but has a low permeability.

As materials forming the low air-permeability layer, a homopolymer or copolymer of vinylidene chloride (which may be hereinafter generically referred to as "polyvinylidene chloride") may be preferably mentioned. Among such copolymers, a vinylidene chloride copolymer where the content of vinylidene chloride is preferably in a range from 50 to 98% by mol, more preferably in a range from 75 to 96% by mol, is preferable because of being excellent in a balance between a film formation property and gas barrier property. As the monomer copolymerizable with vinylidene chloride, specifically for example, vinyl chloride, acrylic acid esters such as methyl acrylate, ethyl acrylate, butyl acrylate, 2-ethylhexyl acrylate and 2-hydroxyethyl acrylate, methacrylic acid esters such as methyl methacrylate and glycidyl methacrylate, acrylonitrile, methacrylonitrile, and unsaturated carboxylic acids such as acrylic acid, methacrylic acid, itaconic acid, and maleic acid can be selected and used singly or in combinations of two or more. Among them, vinyl chloride or acrylic acid ester is preferably used in terms of a film formation property. The low air-permeability layer may be constituted by appropriate combinations of one type or two or more types of polyvinylidene chloride, and further by any combination where any publicly known additive such as a heat stabilizer, a light stabilizer, and a lubricant is appropriately added.

The thickness of the low air-permeability layer is not particularly limited, may be appropriately set depending on the desired oxygen gas barrier property and the like, and is preferably 0.5 to 30 µm, more preferably 0.8 to 10 µm, and most preferably 1 to 2 µm.

The polyvinylidene chloride is usually used as an emulsion or a solution. The low air-permeability portion can be formed by, for example, a method where the polyvinylidene chloride resin which is, if necessary, dissolved or dispersed in a solvent and thus formed into an application liquid is applied onto the surface of the first substrate.

The air-impermeable layer is a layer which blocks permeation of oxygen gas, water vapor, and hydrogen gas.

Metal or metal oxide may be mentioned preferably as the material for constituting the air-impermeable layer. As metals, specifically, aluminum, gold, silver, copper, nickel, chromium, germanium, selenium, titanium, tin, zinc, etc. may be mentioned. As metal oxides, specifically, aluminum oxide, silicon oxide, etc. may be mentioned. As the metal or metal oxide, aluminum, aluminum oxide, or silicon oxide is preferable in terms of economic efficiency, more preferably aluminum is preferable in terms of a gas barrier property, economic efficiency, stability and practicality.

These metal or metal oxides are vapor-deposited on the second substrate by, for example, using a publicly known method such as a vacuum deposition method, a sputtering method, an ion plating method, and the like, or placing a metal foil, and thus the air-impermeable portion can be formed. The thickness of the air-impermeable layer which is a vapor-deposited film or a metal foil is preferably 50 to 5000 angstroms, more preferably 100 to 1000 angstroms, and most preferably 200 to 800 angstroms.

As the sealant layer, in general, thermal fusible resins used in an outer bag for disposable body warmer packaging can be used without limitation. For example, low density polyethylene, medium density polyethylene, high density polyethylene, straight-chain (linear) low density polyethylene, polypropylene, an ethylene-vinyl acetate copolymer, an ionomer resin, an ethylene-ethyl acrylate copolymer, an ethylene-acrylic acid copolymer, an ethylene-methacrylic acid copolymer, an ethylene-propylene copolymer, a methylpentene polymer, and an acid-modified polyolefin-based resin where a polyolefin-based resin such as polyethylene, polystyrene or polypropylene is modified with an unsaturated carboxylic acid such as acrylic acid, methacrylic acid, maleic anhydride or fumaric acid, as well as other resins can be used singly or in combinations of two or more. Various resin films can be produced by a method where one or more of the above various resins are used and such resins are subjected singly or in combinations of two or more to multilayer co-extrusion film formation with an extrusion method, a cast molding method, a T-die method, a cutting method, an inflation method, or other film formation methods. Furthermore, various resin films can be produced by a method where two or more of the resins are used, mixed, and subjected to film formation, or the like. Further, the various resin films can be formed to be uniaxially or biaxially oriented by utilizing, for example, a tentering method or a tubular method. Among them, unoriented polypropylene, biaxially oriented polypropylene, unoriented polyethylene, low density polyethylene, medium density polyethylene, high density polyethylene or straight-chain (linear) low density polyethylene is preferable, and in particular, unoriented polypropylene, biaxially oriented polypropylene or straight-chain (linear) low density polyethylene is more preferable in terms of a thermal fusion property. The thickness of the sealant layer is preferably 5 to 300 µm, more preferably 10 to 100 µm, and most preferably 15 to 50 µm.

An adhesive layer is preferably provided between the air-impermeable layer and the low air-permeability layer so that they are laminated on the sealant layer. As the adhesive forming the adhesive layer, any adhesive usually used in the outer bag for disposable body warmer packaging can be used without any limitation, and for example, an ether-based adhesive, a polyvinyl acetate-based adhesive, polyacrylic acid ester-based adhesive made of a homopolymer of acrylic acid ethyl, butyl or 2-ethylhexyl ester, or a copolymer thereof with methyl methacrylate, acrylonitrile, styrene or the like, a cyanoacrylate-based adhesive, an ethylene copolymer-based adhesive made of a copolymer of ethylene with a monomer such as vinyl acetate, ethyl acrylate, acrylic acid or methacrylic acid, a cellulose-based adhesive, a polyester-based adhesive, a polyamide-based adhesive, a polyimide-based adhesive, an amino resin-based adhesive made of a urea resin, a melamine resin or the like, a phenol resin-based adhesive, an epoxy-based adhesive, a polyurethane-based adhesive, a reaction (meth)acrylic-based adhesive, a rubber-based adhesive made of a chloroprene rubber, a nitrile rubber, a styrene-butadiene rubber or the like, a silicone-based adhesive, an inorganic adhesive made of alkali metal silicate, low melting point glass or the like, or other adhesives can be used. The composition form of the adhesive may be any composition form such as an aqueous form, a solution form, an emulsion form, and a dispersion form. Also, the form of the adhesive may be any form such as a film-sheet form, a powder form, and a solid form. Furthermore, the adhesion mechanism may be any mechanism such as chemical reaction, solvent volatilization, thermal fusion, and thermal pressure mechanisms. Any mode usually used can be used as a usage mode of the adhesive without any limitation, and the adhesive layer can be formed by, for example, applying the adhesive onto at least one of the individual layers by a roll coating method, a gravure roll coating method, a kiss coating method, other coating methods, a printing method or the like, and then drying a solvent and the like. The content the adhesive is preferably 0.1 to 10 g/m$^2$ (dry state), more preferably 0.5 to 8 g/m$^2$ (dry state), and most preferably 1.5 to 4 g/m$^2$ (dry state).

In the outer bag for disposable body warmer packaging of the present invention, a printing ink layer may be provided as a constituent at any location. The printing ink layer can be formed by adding one or more usual ink vehicles as a main component, optionally adding, if necessary, one or two or more additives such as a plasticizer, a stabilizer, an antioxidant, a light stabilizer, an ultraviolet ray absorber, a curing agent, a crosslinking agent, a lubricant, an antistatic agent and a filler thereto, further adding a colorant such as a dye/pigment thereto, and sufficiently kneading the resultant with a solvent, a diluent or the like to prepare an ink composition; and then printing a desired character, graphic, sign, pattern, and the like with the ink composition by use of, for example, gravure printing, offset printing, relief printing, screen printing, transfer printing, flexographic printing, or other printing schemes.

Any ink vehicle usually used for the outer bag for disposable body warmer packaging can be used as the ink vehicle without any limitation, examples of which may include, flaxseed oil, tung oil, soybean oil, hydrocarbon oil, rosin, rosin ester, a rosin-modified resin, shellac, an alkyd resin, a phenol-based resin, a maleic acid resin, a natural resin, a hydrocarbon resin, a polyvinyl chloride-based resin, a polyvinyl acetate-based resin, a polystyrene-based resin, a polyvinyl butyral resin, an acrylic or methacrylic-based resin, a polyamide-based resin, a polyester-based resin, a polyurethane-based resin, an epoxy-based resin, a urea resin, a melamine resin, an amino alkyd-based resin, nitrocellulose, ethyl cellulose, a chlorinated rubber and a cyclized rubber singly or in combinations of two or more. The content of the printing ink layer is preferably 0.1 to 10 g/m² (dry state), more preferably 0.5 to 8 g/m² (dry state), and most preferably 1 to 5 g/m² (dry state).

The outer bag for disposable body warmer packaging of the present invention may further include an additional resin layer. The additional resin layer may be a layer formed from any resin as long as a gas permeation property and water vapor permeation property of the outer bag for disposable body warmer packaging of the present invention are not impaired, and can be provided at any desired position depending on the characteristics of the resin. For example, when the thermal fusible resin which has been described above as being usable in the sealant layer is to be used in the additional resin layer, it can be provided outward against the sealant layer and function as a heat-sealed portion in formation of an outer bag. Also, when the heat-resistant resin which has been described above as being usable in the first and second substrates is to be used in the additional resin layer, it can be provided between the first and second substrates so as to enhance the strength of the multilayer film, or provided opposite to the sealant layer and at a position corresponding to the outer surface of outer bag for disposable body warmer packaging so as to function as a protection film. The thickness of the additional resin layer is not particularly limited, and is preferably 3 to 500 µm, more preferably 5 to 300 µm, further preferably 5 to 100 µm, most preferably 5 to 50 µm.

The outer bag for disposable body warmer packaging of the present invention can achieve the seal strength of preferably 15.0 N/15 mm or larger, more preferably 20.0 N/15 mm or larger, and most preferably 25.0 N/15 mm or larger. By defining the seal strength of the outer bag for disposable body warmer packaging of the present invention within the above-identified numerical ranges, it is made possible to achieve the effect that the outer bag is not easily opened or broken even when a large impact acts upon the outer bag from outside.

First Embodiment

In the first embodiment, the low air-permeability layer and the air-impermeable layer are provided on one sealant layer. The low air-permeability portion has the low air-permeability layer. The air-impermeable portion has the low air-permeability layer and the air-impermeable layer. The low air-permeability layer is laminated on the sealant layer. The air-impermeable layer is laminated partly on the low air-permeability layer. Those that have been described above can be used without any limitation as the substrate, the low air-permeability layer and the air-impermeable layer, the sealant layer, and the like.

In the first embodiment, the portion where the low air-permeability layer and the air-impermeable layer are laminated constitutes the air-impermeable portion. The portion where the air-impermeable layer is not laminated constitutes the low air-permeability portion.

The features of the outer bag for disposable body warmer packaging according to the first embodiment will be described with reference to FIGS. 1A to 1C.

FIG. 1A is a cross-sectional view. FIG. 1B(a) is a plan view where the outer bag is viewed in the direction of an arrow X1 in FIG. 1A. FIG. 1B(b) is a plan view where the outer bag is viewed in the direction of an arrow Y1 in FIG. 1A. FIG. 1C is a cross-sectional view illustrating a laminated state in the layered portion indicated by E1 in FIG. 1A.

In the first embodiment, a laminated sheet is formed by laminating the first multilayer film A1 on one sealant layer 30 over the entire area of the sealant layer 30 and laminating the second multilayer film B1 on a region except for the peripheral portion of the first multilayer film A1. The laminated sheet is wound such that the sealant layer 30 becomes the inner surface's side of the outer bag and the second multilayer film B1 becomes the outer surface's side of the outer bag. The peripheral portion of the laminated sheet is three-side pillow-sealed, and thus the bag can be formed. The space in the bag becomes the accommodating portion of the disposable body warmer. Both ends of the laminated sheet do not include the second multilayer film B1.

In FIG. 1A, the heat-sealed portion is indicated by C1.

Figure 1B:
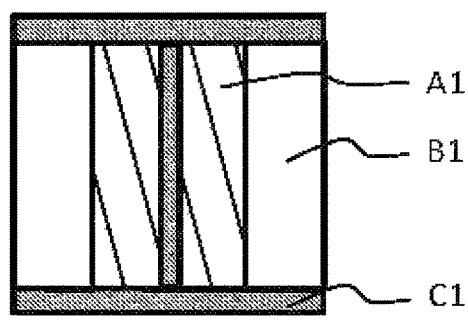
FIG. 1B is a plan view of the outer bag for disposable body warmer packaging in the Embodiment 1 of the present invention, where (a) is a plan view where the outer bag is viewed in the direction of an arrow X1 in FIG. 1A and (b) is a plan view where the outer bag is viewed in the direction of an arrow Y1 in FIG. 1A.
Figure 1B:
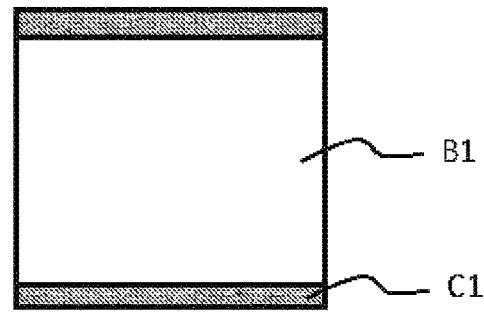
Figure 1C:
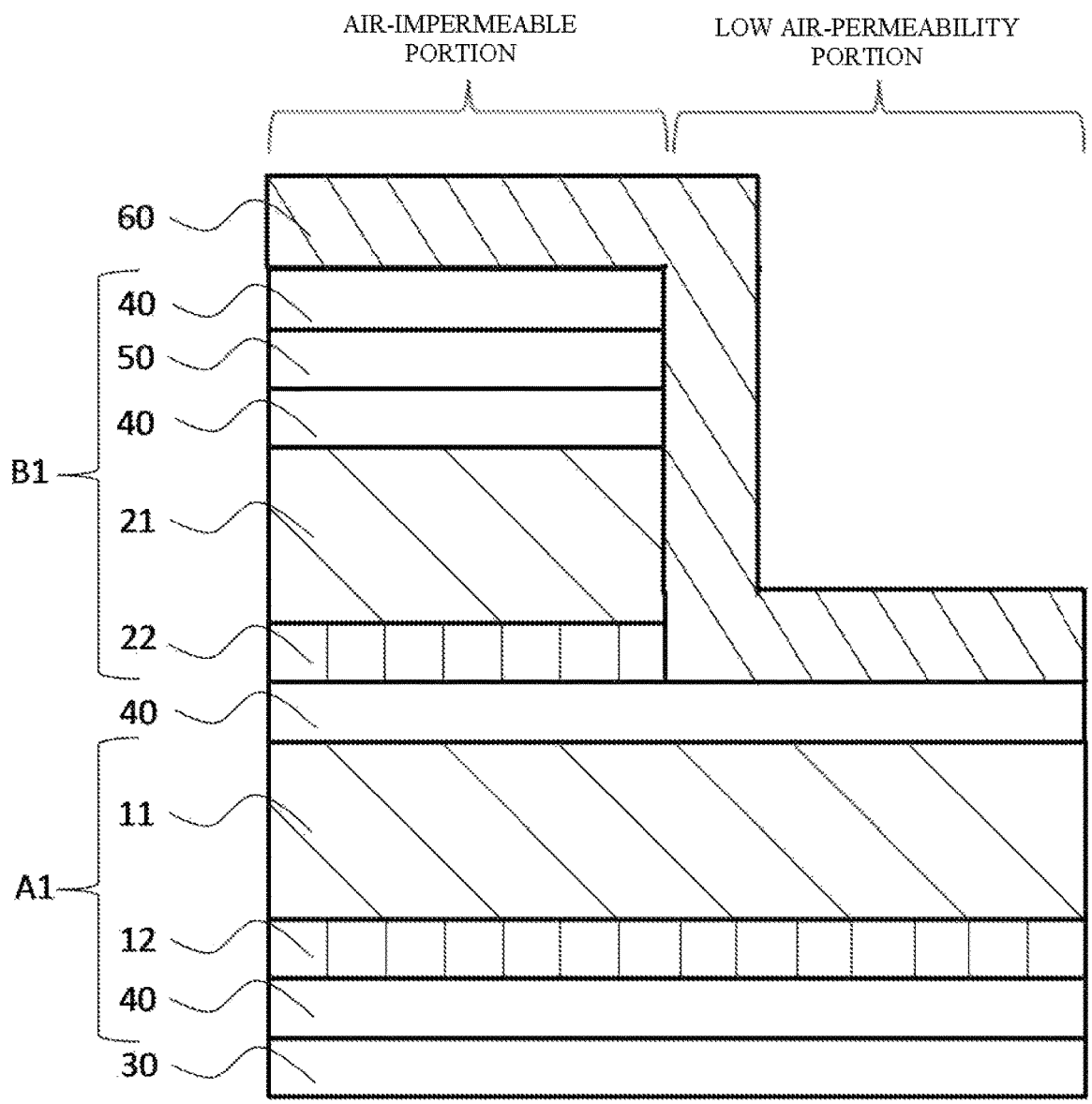
FIG. 1C is an explanatory view illustrating a layered structure of a cross section of a layered portion (E1 in FIG. 3A) of the outer bag for disposable body warmer packaging in the Embodiment 1 of the present invention.

FIG. 1C illustrates the layered structure of the first multilayer film A1 and the second multilayer film B1 in the layered portion E1 illustrated in FIG. 1A. The portion where the second multilayer film B1 is laminated on the first multilayer film A1 laminated on the sealant layer 30 becomes the air-impermeable portion. The portion where only the first multilayer film A1 is laminated and the second multilayer film B1 is not laminated becomes the low air-permeability portion. The air-impermeable portion is obtained by laminating, an additional resin layer 60, an adhesive layer 40, a printing ink layer 50, an adhesive layer 40, a second heat-resistant resin substrate 21, a vapor-deposited layer (air-impermeable layer) 22, an adhesive layer 40, a first heat-resistant resin substrate 11, a polyvinylidene chloride layer (low air-permeability layer) 12, an adhesive layer 40, and a sealant layer 30 when viewed from the outer surface's side of the outer bag. The low air-permeability portion is obtained by laminating an additional resin layer 60, an adhesive layer 40, a first heat-resistant resin substrate 11, a polyvinylidene chloride layer (low air-permeability layer) 12, an adhesive layer 40, and a sealant layer 30 when viewed from the outer surface's side of the outer bag and, depending on the cases, a printing ink layer 50, an adhesive layer 40, and an additional resin layer 60 may be further laminated on the first heat-resistant resin substrate 11. The area of the low air-permeability portion can be adjusted by changing the area where the second multilayer film B1 is laminated. The "ratio of the area of the low air-permeability portion to the total internal area of the accommodating portion" refers to a ratio of the area of the low air-permeability portion to the area of the inside of the bag except for the heat-sealed portion. In FIGS. 1A to 1C, the second multilayer film B1 is laminated on the most part of the area of the first multilayer film A1 except for both ends thereof, and the ratio of the area of the low air-permeability portion to the total internal area of the accommodating portion is 15%.

Second Embodiment

The second embodiment is a modified example of the first embodiment. In the same manner as in the first embodiment, the low air-permeability layer and the air-impermeable layer are provided on one sealant layer 30. The low air-permeability portion has the low air-permeability layer. The air-impermeable portion has the low air-permeability layer and the air-impermeable layer. Those that have been described above can be used without any limitation as the substrate, the low air-permeability layer and the air-impermeable layer, the sealant layer 30, and the like. In the second embodiment, the portion where the low air-permeability layer and the air-impermeable layer is laminated on the one sealant layer constitutes the air-impermeable portion. The portion where the air-impermeable layer is not laminated constitutes the low air-permeability portion.

The features of the outer bag for disposable body warmer packaging according to the second embodiment will be described with reference to FIGS. 2A to 2C.

Figure 2A:
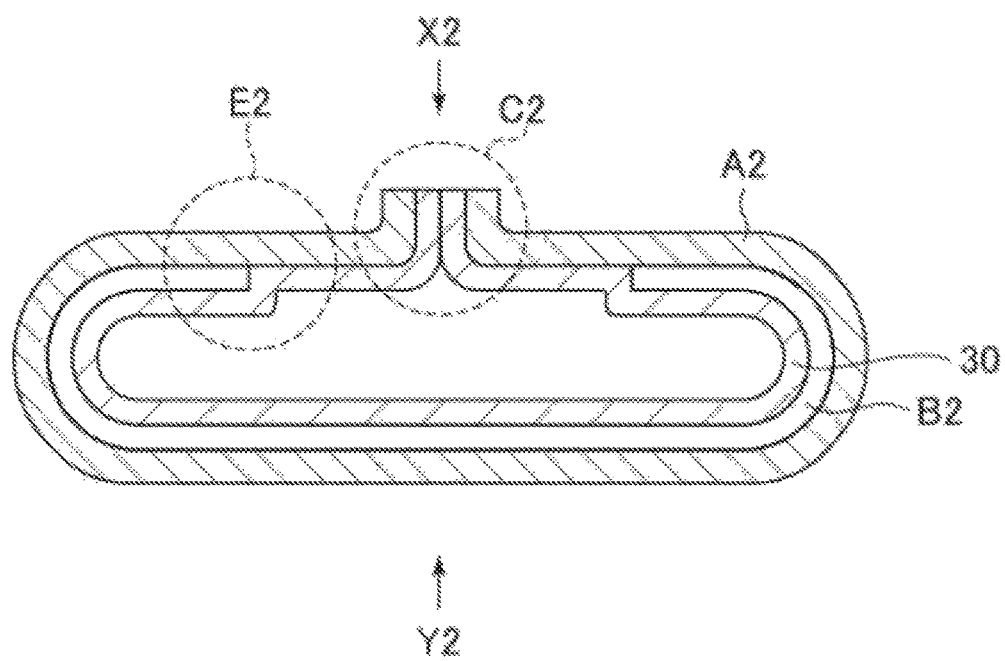
FIG. 2A is a cross-sectional view of an outer bag for disposable body warmer packaging in Embodiment 2 of the present invention.
Figure 2B:
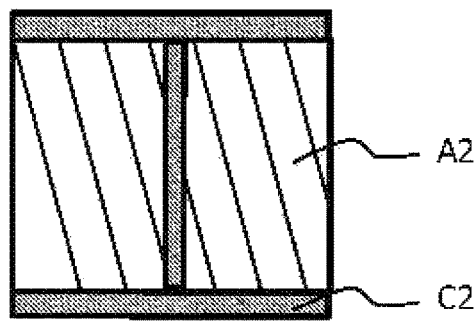
FIG. 2B is a plan view of the outer bag for disposable body warmer packaging in the Embodiment 2 of the present invention, where (a) is a plan view where the outer bag is viewed in the direction of an arrow X2 in FIG. 2A and (b) is a plan view where the outer bag is viewed in the direction of an arrow Y2 in FIG. 2A.
Figure 2B:
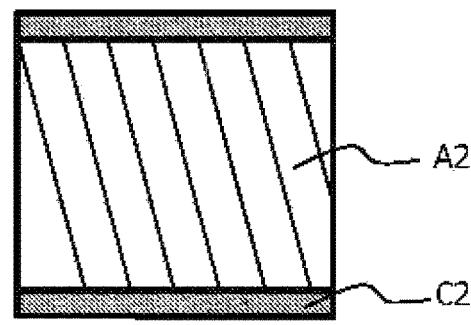

FIG. 2A is a cross-sectional view. FIG. 2B(a) is a plan view where the outer bag is viewed in the direction of an arrow X2 in FIG. 2A. FIG. 2B(b) is a plan view where the outer bag is viewed in the direction of an arrow Y2 in FIG. 2A. FIG. 2C is a cross-sectional view illustrating a laminated state in the layered portion indicated by E2 in FIG. 2A.

In the second embodiment, a laminated sheet is obtained by laminating the second multilayer film B2 on a region of the sealant layer 30 except for the peripheral portion of the sealant layer 30 and laminating the first multilayer film A2 having the same size as the entire area of the sealant layer 30 on the second multilayer film B2 and the sealant layer 30. The laminated sheet is wound such that the first multilayer film A2 becomes the outer surface's side of the outer bag and the sealant layer 30 becomes the inner surface's side of the outer bag. The peripheral portion of the laminated sheet three-side pillow-sealed, and thus the bag thus can be formed. The space in the bag becomes the accommodating portion of the disposable body warmer. Both ends of the laminated sheet does not include the second multilayer film B2.

In FIG. 2A, the heat-sealed portion is indicated by C2.

Figure 2C:
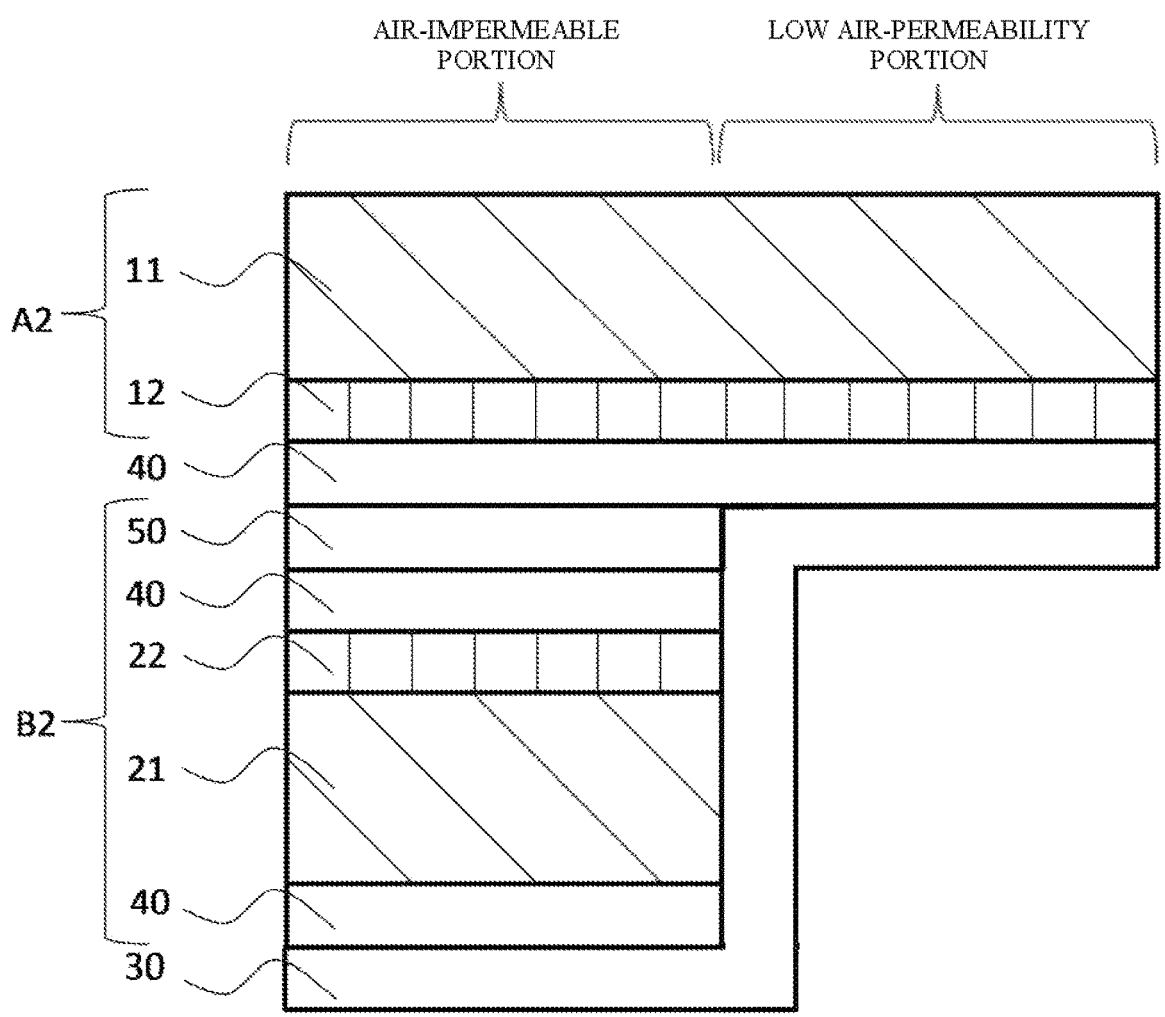
FIG. 2C is an explanatory view of a layered structure of a cross section of a layered portion (E2 in FIG. 2A) of the outer bag for disposable body warmer packaging in the Embodiment 2 of the present invention.

FIG. 2C illustrates a layered structure of the first multilayer film A2 and the second multilayer film B2 in the layered portion E2 indicated in FIG. 2A. The second multilayer film B2 is laminated on a region except for both ends and their neighborhood of the sealant layer 30. The first multilayer film A2 of the same area as that of the sealant layer 30 is laminated on the second multilayer film B2 and the sealant layer 30. The portion where the first multilayer film A2 and the second multilayer film B2 are laminated becomes the air-impermeable portion. The portion where the second multilayer film B2 is not laminated becomes the low air-permeability portion. As illustrated in FIG. 2C, the air-impermeable portion is constituted by laminating, when viewed from the outer surface's side of the outer bag, the first heat-resistant resin substrate 11, the polyvinylidene chloride layer (low air-permeability layer) 12, the adhesive layer 40, the printing ink layer 50, the adhesive layer 40, the vapor-deposited layer (air-impermeable layer) 22, the second heat-resistant resin substrate 21, the adhesive layer 40, and the sealant layer 30. The low air-permeability portion is constituted by laminating, when viewed from the outer surface's side of the outer bag, the first heat-resistant resin substrate 11, the polyvinylidene chloride layer (low air-permeability layer) 12, and the sealant layer 30. Depending on the cases, the low air-permeability portion may be configured such that an adhesive layer 40, a printing ink layer 50, and an adhesive layer 40 are further provided between the polyvinylidene chloride layer 12 and the sealant layer 30. The area of the low air-permeability portion can be adjusted by changing the area where the second multilayer film B2 is laminated. In FIGS. 2A to 2C, the second multilayer film B2 is laminated on the most part of the region except for both ends and their neighborhood of the sealant layer 30. The ratio of the area of the low air-permeability portion to the total internal area of the accommodating portion is 15%.

Third Embodiment

The third embodiment is a modified example of the first embodiment. In the same manner as in the first embodiment, the low air-permeability layer and the air-impermeable layer are provided on one sealant layer 30. The low air-permeability portion has the low air-permeability layer. The air-impermeable portion has the low air-permeability layer and the air-impermeable layer. Those that have been described above can be used without any limitation as the substrate, the low air-permeability layer and the air-impermeable layer, the sealant layer, and the like. In the third embodiment, one laminated sheet is wound and stacked each other and the peripheral portion thereof is three-side sealed. The portion where the low air-permeability layer and the air-impermeable layer are laminated constitutes the air-impermeable portion. The portion where the air-impermeable layer is not laminated constitutes the low air-permeability portion.

The features of the outer bag for disposable body warmer packaging according to the third embodiment will be described with reference to FIGS. 3A to 3C.

Figure 3A:
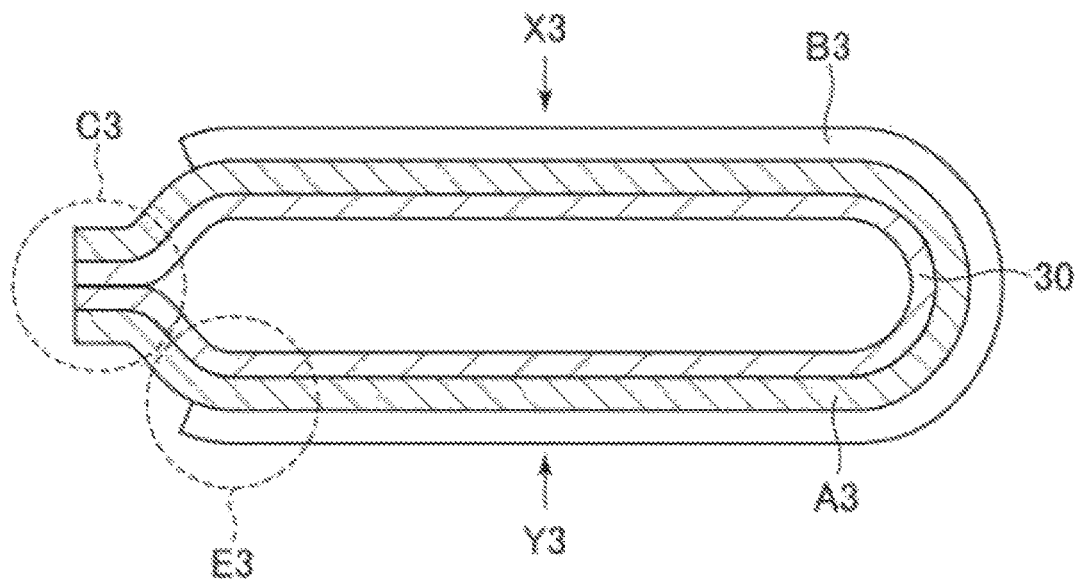
FIG. 3A is a cross-sectional view of an outer bag for disposable body warmer packaging of Embodiment 3 of the present invention.

FIG. 3A is a cross-sectional view. FIG. 3B(a) is a plan view where the outer bag is viewed in the direction of an arrow X3 in FIG. 3A. FIG. 3B(b) is a plan view where the outer bag is viewed in the direction of an arrow Y3 in FIG. 3A. FIG. 3C is a cross-sectional view illustrating a laminated state in the layered portion of a region including the neighborhood of the heat-sealed portion indicated by E3 in FIG. 3A.

In the third embodiment, a laminated sheet is obtained by laminating the first multilayer film A3 on the sealant layer 30 over the entire area of the sealant layer 30 and laminating the second multilayer film B3 in a region except for the peripheral portion of the first multilayer film A3. The laminated sheet is wound such that the sealant layer 30 is on the inner surface's side of the outer bag and the second multilayer film B3 is on the outer surface's side of the outer bag. Both ends of the laminated sheet are stacked each other. The peripheral portion thereof is three-side sealed, and thus a bag can be formed. The space in the bag becomes the accommodating portion of the disposable body warmer. Both ends of the laminated sheet does not include the second multilayer film B3.

In FIG. 3A, the heat-sealed portion is indicated by C3.

Figure 3B:
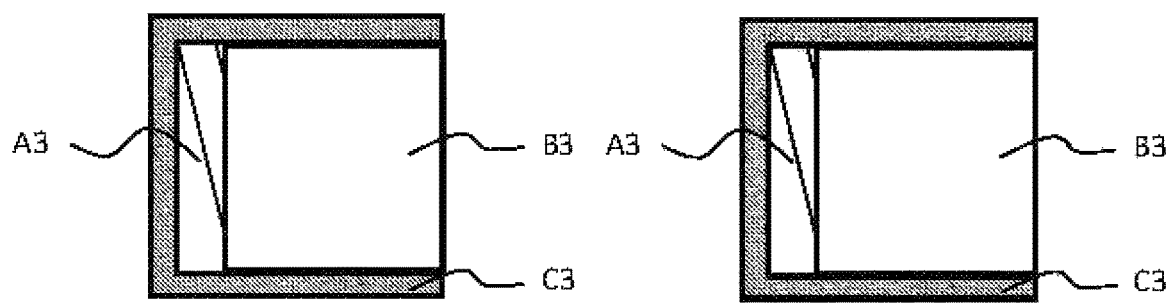
FIG. 3B is a plan view of the outer bag for disposable body warmer packaging in the Embodiment 3 of the present invention, where (a) is a plan view where the outer bag is viewed in the direction of an arrow X3 in FIG. 3A and (b) is a plan view where the outer bag is viewed in the direction of an arrow Y3 in FIG. 3A.
Figure 3C:
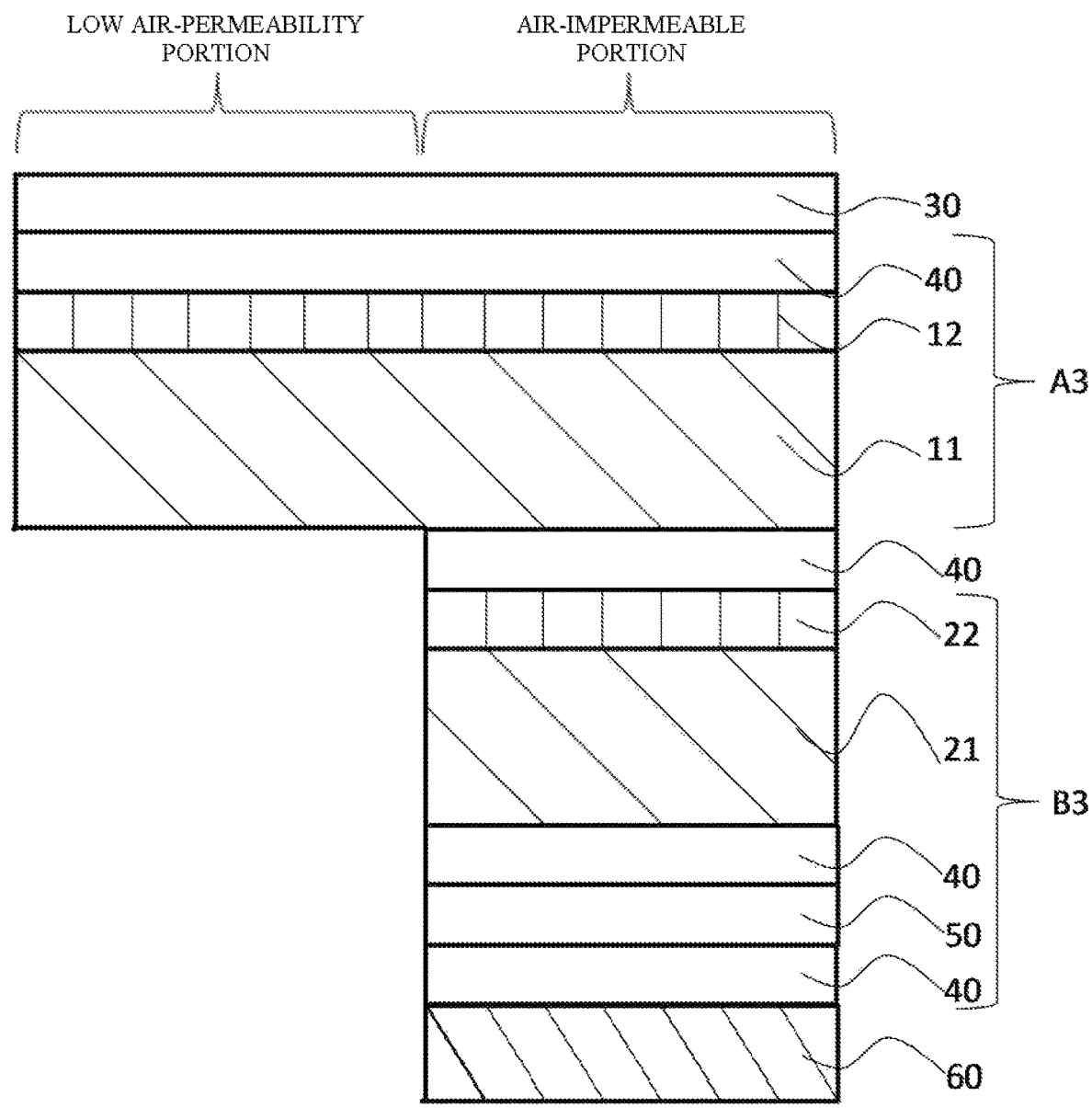
FIG. 3C is an explanatory view illustrating a layered structure of a cross section of a layered portion (E3 in FIG. 3A) of the outer bag for disposable body warmer packaging in the Embodiment 3 of the present invention.

FIG. 3C illustrates the layered structure of a cross section of the layered portion E3 in the neighborhood of the heat-sealed portion illustrated in FIG. 3A. In FIG. 3C, the air-impermeable portion is constituted by laminating, when viewed from the outer surface's side of the outer bag, the an additional resin layer 60, the adhesive layer 40, the printing ink layer 50, adhesive layer 40, the second heat-resistant resin substrate 21, the vapor-deposited layer (air-impermeable layer) 22, the adhesive layer 40, the first heat-resistant resin substrate 11, the polyvinylidene chloride layer (low air-permeability layer) 12, the adhesive layer 40, and the sealant layer 30. In FIG. 3C, the low air-permeability portion adjacent to the heat-sealed portion of the laminated sheet is constituted by laminating, when viewed from the outer surface's side of the outer bag, the first heat-resistant resin substrate 11, the polyvinylidene chloride layer (low air-permeability layer) 12, the adhesive layer 40, and the sealant layer 30. In the low air-permeability portion, an adhesive layer 40, a printing ink layer 50, an adhesive layer 40, and an additional resin layer 60 may be further laminated on the outer side of the first heat-resistant resin layer 11.

The area of the low air-permeability portion can be adjusted by changing the area where the second multilayer film B3 is laminated. In FIG. 3A to 3C, the laminated sheet is formed by laminating the second multilayer film B3 on the most part of the region except for the region including peripheral portions of the sealant layer 30 and the first multilayer film layer A3. Both ends of one laminated sheet are stacked each other so as to be heat-sealed. According to the implementation illustrated in FIGS. 3A to 3C, the ratio of the area of the low air-permeability portion to the total internal area of the accommodating portion is 15%.

The second multilayer film B3 is provided on the outer surface's side of the outer bag for disposable body warmer packaging in FIGS. 3A to 3C. However, the first multilayer film A3 may be provided on the outer surface's side of the outer bag for disposable body warmer packaging in the same manner as the outer bag for disposable body warmer packaging of the first embodiment.

Fourth Embodiment

The fourth embodiment is a modified example of the third embodiment. The low air-permeability layer and the air-impermeable layer are provided on one sealant layer 30. The low air-permeability portion has the low air-permeability layer. The air-impermeable portion has the low air-permeability layer and the air-impermeable layer. Those that have been described above can be used without any limitation as the substrate, the low air-permeability layer and the air-impermeable layer, the sealant layer, and the like. In the fourth embodiment, two laminated sheets are stacked each other, and the peripheral portion thereof is four-side sealed. The portion where the low air-permeability layer and the air-impermeable layer are laminated constitutes the air-impermeable portion. The portion where the air-impermeable layer is not laminated constitutes the low air-permeability portion.

The features of the outer bag for disposable body warmer packaging according to the fourth embodiment will be described with reference to FIGS. 4A to 4C.

Figure 4A:
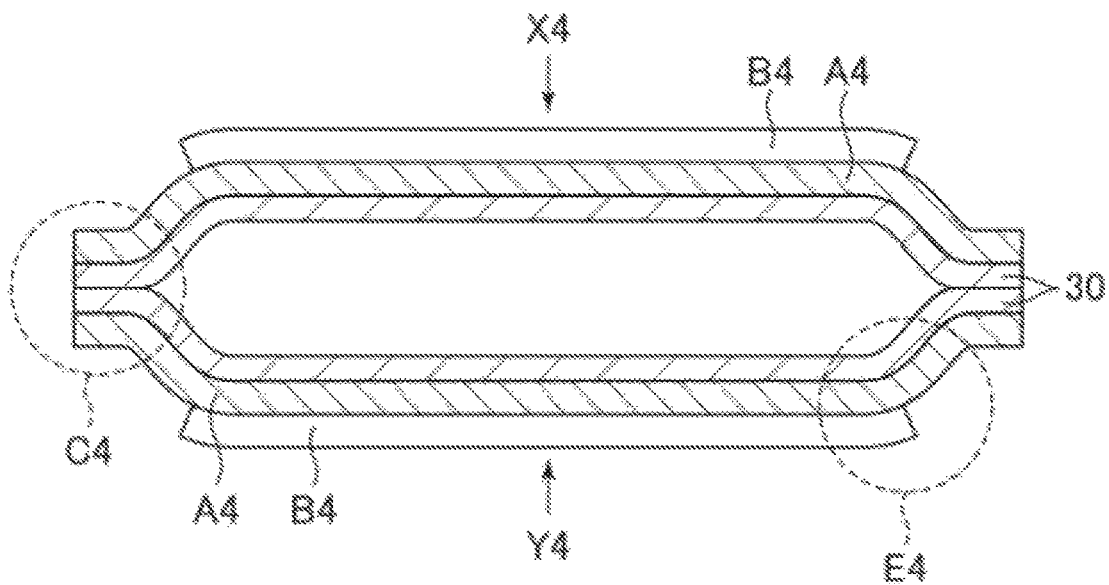
FIG. 4A is a cross-sectional view of an outer bag for disposable body warmer packaging in Embodiment 4 of the present invention.

FIG. 4A is a cross-sectional view. FIG. 4B(a) is a plan view where the outer bag is viewed in the direction of an arrow X4 in FIG. 4A. FIG. 4B(b) is a plan view where the outer bag is viewed in the direction of an arrow Y4 in FIG. 4A. FIG. 4C is a cross-sectional view illustrating a laminated state in the layered portion of a region including the neighborhood of the heat-sealed portion indicated by E4 in FIG. 4A.

In the fourth embodiment, a laminated sheet is formed by laminating the first multilayer film A4 on the sealant layer 30 over the entire area of the sealant layer 30 and laminating the second multilayer film B4 in a region at the central portion except for the peripheral portion of the first multilayer film A4. The two laminated sheets are stacked each other, and the peripheral portion thereof is four-side sealed and thus a bag can be formed. The space in the bag becomes the accommodating portion of the disposable body warmer. The region adjacent to the heat-sealed portion does not include the second multilayer film B4. According to the implementation illustrated in FIGS. 4A to 4C, the two laminated sheets are stacked each other such that the sealant layer 30 is positioned on the inner surface's side of the outer bag and the second multilayer film B4 is positioned on the outer surface's side of the outer bag.

In FIG. 4A, the heat-sealed portion is indicated by C4.

Figure 4B:
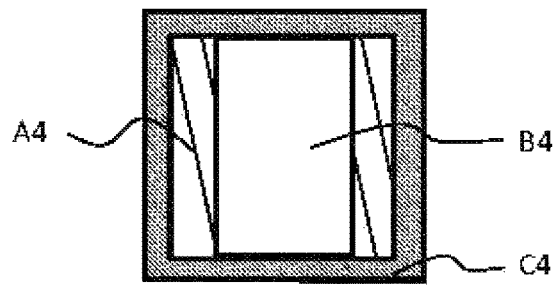
FIG. 4B is a plan view of the outer bag for disposable body warmer packaging in the Embodiment 4 of the present invention, where (a) is a plan view where the outer bag is viewed in the direction of an arrow X4 in FIG. 4A and (b) is a plan view where the outer bag is viewed in the direction of an arrow Y4 in FIG. 4A.
Figure 4B:
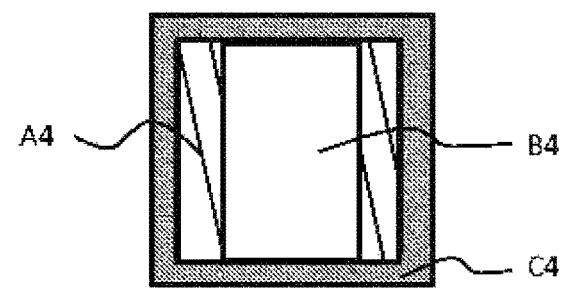
Figure 4C:
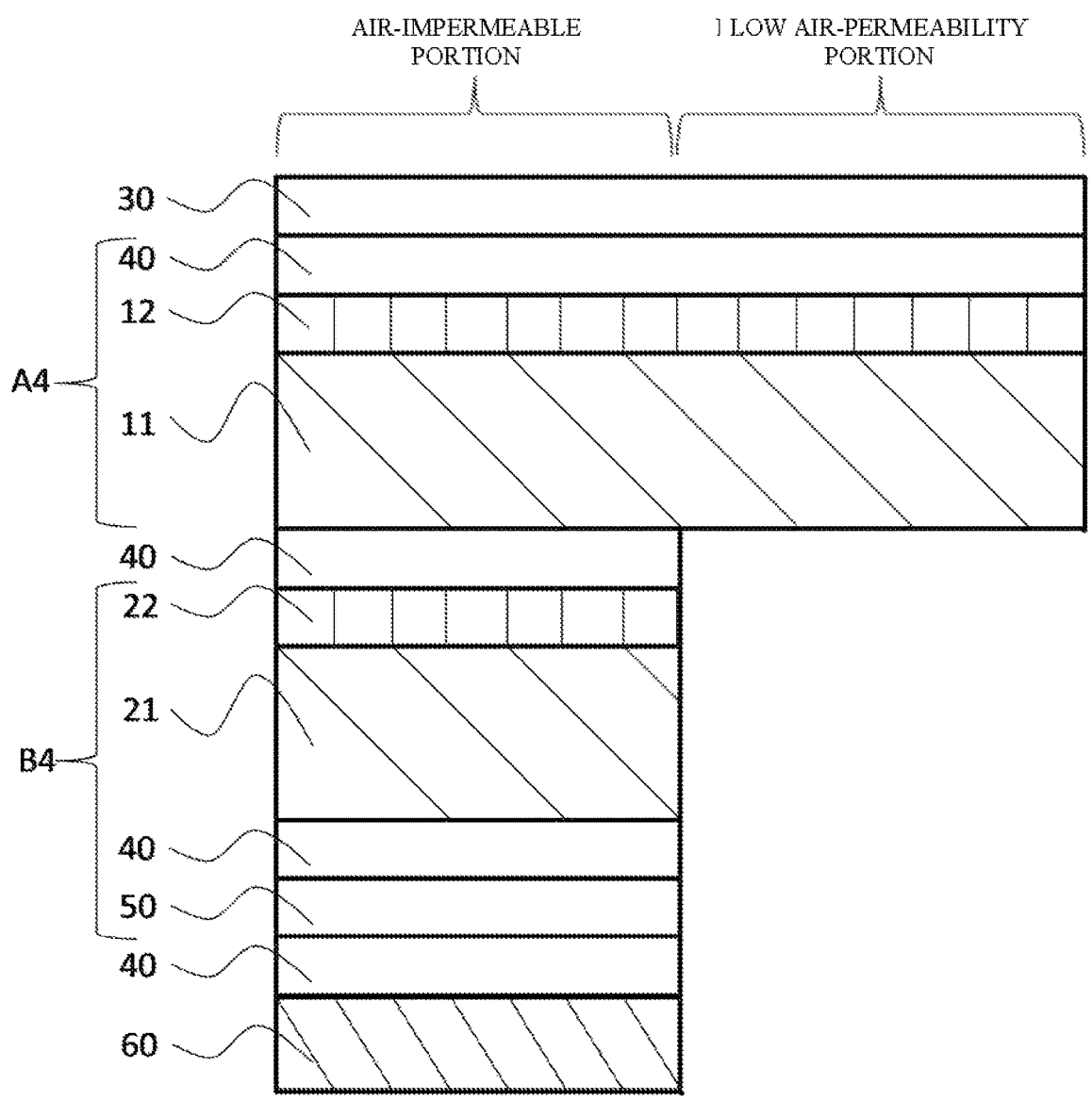
FIG. 4C is an explanatory view illustrating a layered structure of a cross section of a layered portion (E4 in FIG. 4A) of the outer bag for disposable body warmer packaging in the Embodiment 4 of the present invention.

As illustrated in FIG. 4C, the air-impermeable portion is constituted by laminating, when viewed from the outer surface's side of the outer bag, the additional resin layer 60, the adhesive layer 40, the printing ink layer 50, the adhesive layer 40, the second heat-resistant resin substrate 21, the vapor-deposited layer (air-impermeable layer) 22, the adhesive layer 40, the first heat-resistant resin substrate 11, the polyvinylidene chloride layer (low air-permeability layer) 12, the adhesive layer 40, and the sealant layer 30. In FIG. 4C, the low air-permeability portion adjacent to the heat-sealed portion of the laminated sheet is constituted by laminating, when viewed from the outer surface's side of the outer bag, the first heat-resistant resin substrate 11, the polyvinylidene chloride layer (low air-permeability layer) 12, the adhesive layer 40, and the sealant layer 30. The low air-permeability portion may be configured such that an adhesive layer 40, a printing ink layer 50, an adhesive layer 40, and an additional resin layer 60 are further laminated on the outer surface of the first heat-resistant resin substrate 11.

The area of the low air-permeability portion can be adjusted by changing the area where the second multilayer film B4 is laminated. In FIGS. 4A to 4C, the laminated sheet is formed by laminating the second multilayer film B4 on the most part of the region except for the region including the peripheral portions of the sealant layer 30 and the first multilayer film layer A4. Both ends of the two laminated sheets are stacked each other to be heat-sealed. In the neighborhood of the heat-sealed portion, the second multilayer film B4 is not laminated and the air-impermeable portion does not exist. According to the implementation illustrated in FIGS. 4A to 4C, the ratio of the area of the low air-permeability portion to the total internal area of the accommodating portion is 15%.

The second multilayer film B4 is provided on the outer surface's side of the outer bag for disposable body warmer packaging in FIGS. 4A to 4C. However, the first multilayer film A4 may be provided on the outer surface's side of the outer bag for disposable body warmer packaging in the same manner as in the outer bag for disposable body warmer packaging of the first embodiment.

Fifth Embodiment

In the fifth embodiment, the low air-permeability layer and the air-impermeable layer are provided on one substrate. The low air-permeability portion has the substrate and the low air-permeability layer. The air-impermeable portion has the substrate and the air-impermeable layer. Those that have been described above can be used without any limitation as the substrate, the low air-permeability layer and the air-impermeable layer, the sealant layer, and the others or the like.

Figure 5A:
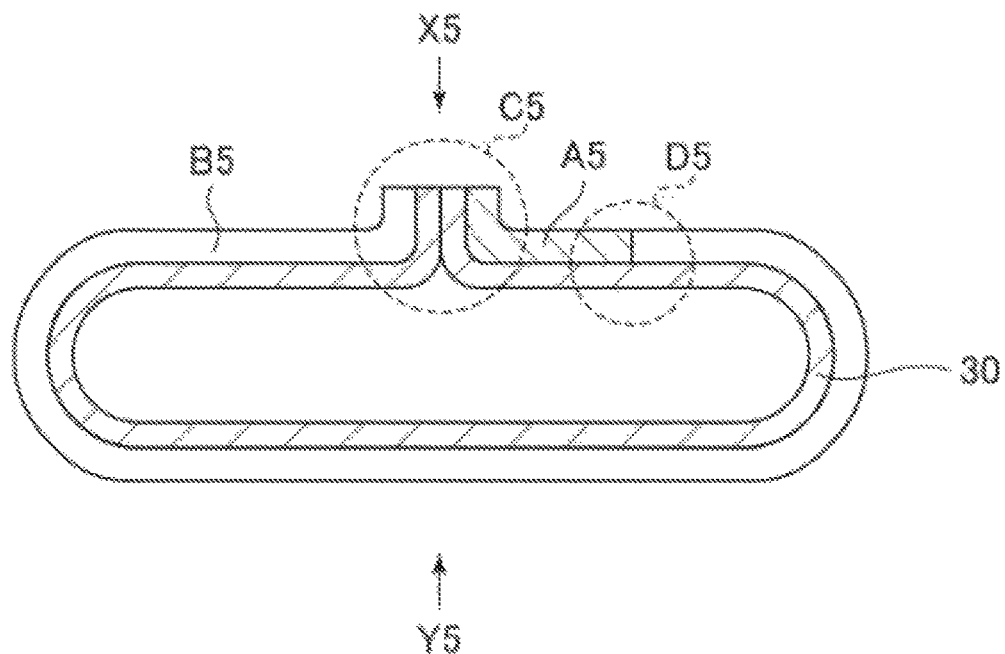
FIG. 5A is a cross-sectional view of the outer bag for disposable body warmer packaging in the Embodiment 5 of the present invention.
Figure 5B:
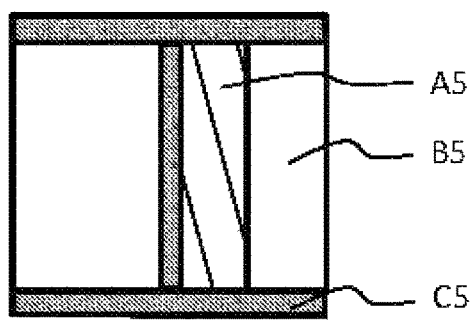
FIG. 5B is a plan view of the outer bag for disposable body warmer packaging in the Embodiment 5 of the present invention, where (a) is a plan view where the outer bag is viewed in the direction of an arrow X5 in FIG. 5A and (b) is a plan view where the outer bag is viewed in the direction of an arrow Y5 in FIG. 5A.
Figure 5B:
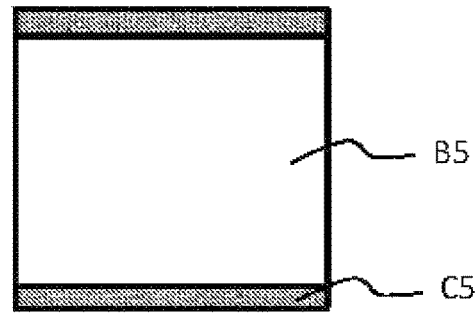
Figure 5C:
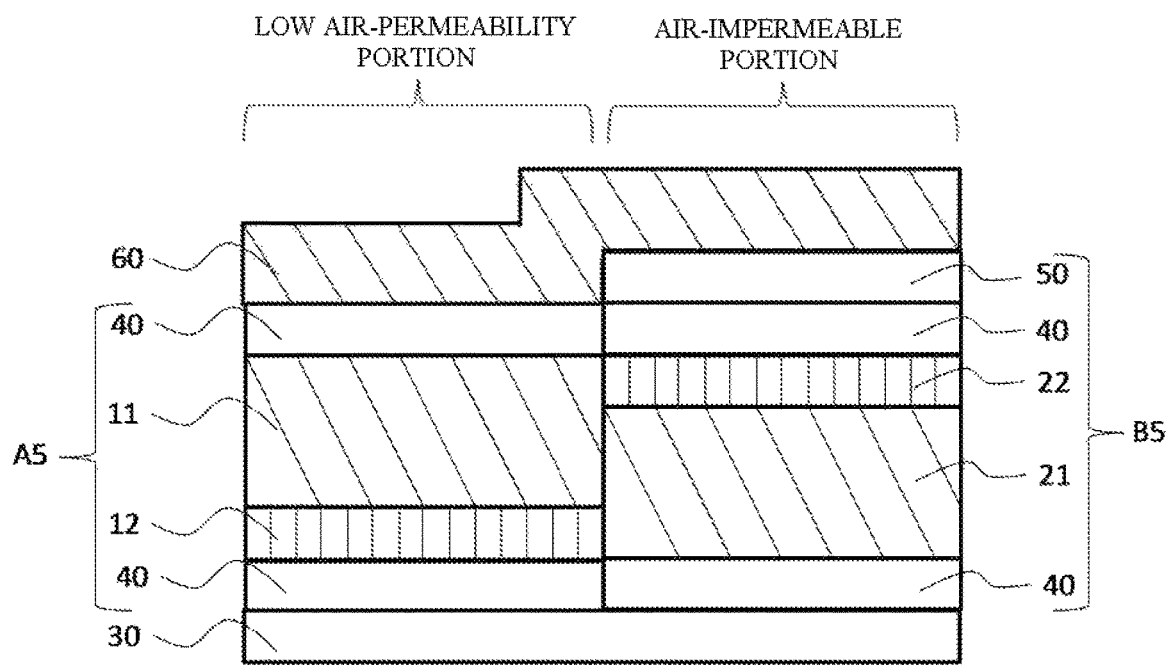
FIG. 5C is an explanatory view illustrating a layered structure of a cross section of a connected portion (D5 in FIG. 5A) of the outer bag for disposable body warmer packaging in the Embodiment 5 of the present invention.
Figure 5D:
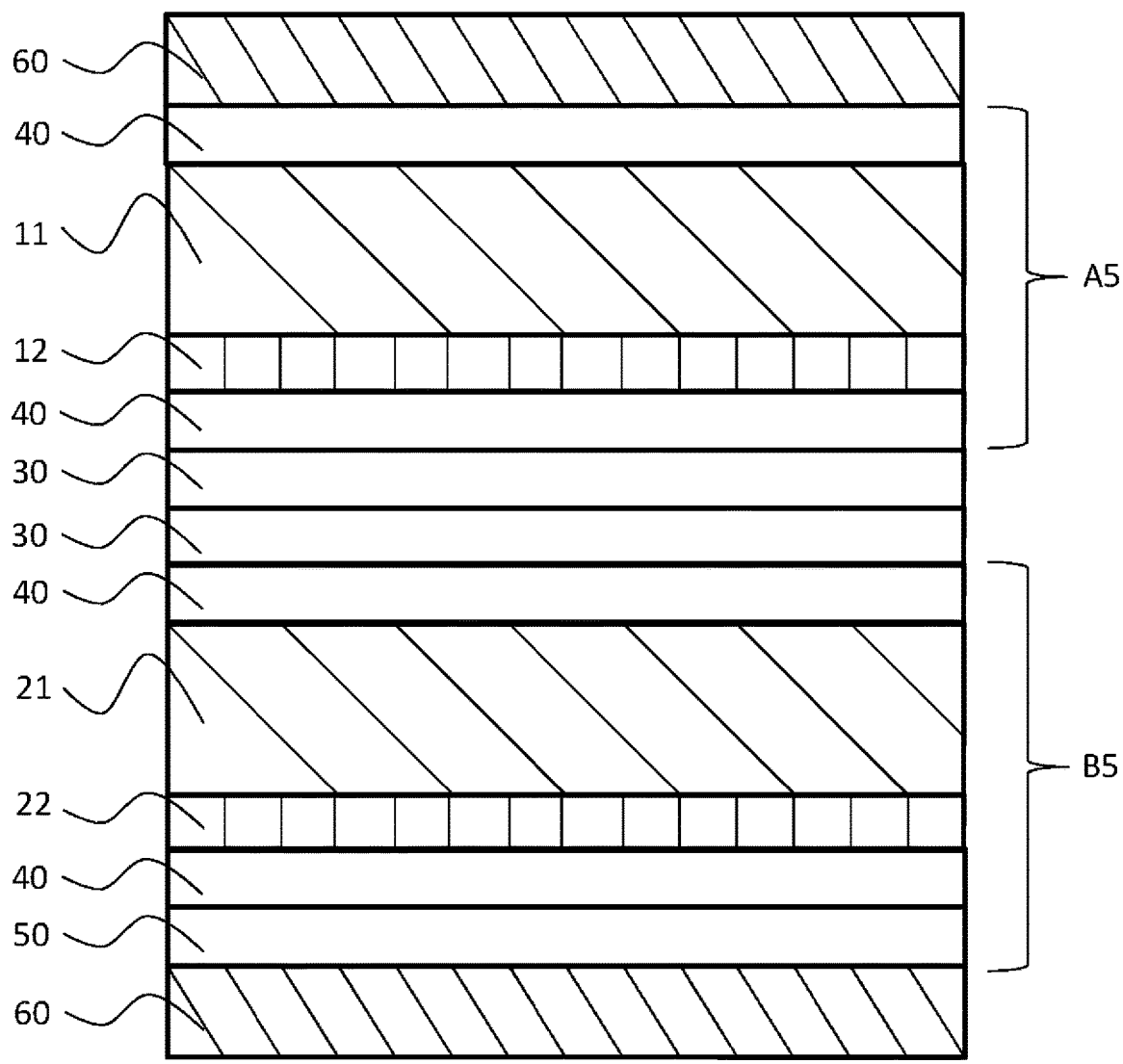
FIG. 5D is an explanatory view illustrating a layered structure of a cross section of a heat-sealed portion (C5 in FIG. 5A) of the outer bag for disposable body warmer packaging in the Embodiment 5 of the present invention.

The features of the outer bag for disposable body warmer packaging according to the fifth embodiment will be described with reference to FIGS. 5A to 5D. FIG. 5A is a cross-sectional view. FIG. 5B(a) is a plan view where the outer bag is viewed in the direction of an arrow X5 in FIG. 5A. FIG. 5B(b) is a plan view where the outer bag is viewed in the direction of an arrow Y5 in FIG. 5A. FIG. 5C is a cross-sectional view illustrating the laminated state in the connected portion indicated by D5 in FIG. 5A. FIG. 5D is a cross-sectional view illustrating the laminated state in the heat-sealed portion indicated by C5 in FIG. 5A.

In the fifth embodiment, according to the outer bag for disposable body warmer packaging of the present invention, the laminated sheet is obtained by joining the first multilayer film A5 and the second multilayer film B5 by the connected portion D5 on one sealant layer 30. The laminated sheet is wound so that the sealant layer 30 becomes the inner surface's side of the outer bag. Both ends of the laminated sheet are stacked each other. The peripheral portion thereof are three-side pillow-sealed, and thus the bag can be formed. The space in the bag becomes the accommodating portion of the disposable body warmer. One end portion of the laminated sheet includes the first multilayer film A5 and the other end portion includes the second multilayer film B5. Accordingly, both ends of the three-side pillow-sealed laminated sheet include the first multilayer film A5 and the second multilayer film B5.

With regard to the connected portion D5, when viewed from the lower layer's side in FIG. 5C, the first multilayer film A5 and the second multilayer film B5 are adjacently laminated on the common sealant layer 30. Common additional resin layer 60 is laminated on the first multilayer film A5 and the second multilayer film B5, and thus the laminated sheet is constituted. The first multilayer film A5 is constituted by laminating, starting from the lower layer, the adhesive layer 40, the polyvinylidene chloride layer 12, the first heat-resistant resin substrate 11, and the adhesive layer 40. The second multilayer film B5 is constituted by laminating, starting from the lower layer, the adhesive layer 40, the second heat-resistant resin substrate 21, the vapor-deposited layer 22, the adhesive layer 40, and the printing ink layer 50.

The heat-sealed portion C5 is obtained by laminating, when viewed from the lower layer of FIG. 5D, the second multilayer film B5, two respective sealant layers 30, and the first multilayer film A5 on the additional resin layer 60. The second multilayer film B5 is constituted by laminating, starting from the lower layer, the printing ink layer 50, the adhesive layer 40, the vapor-deposited layer 22, the second heat-resistant resin substrate 21, and the adhesive layer 40. The first multilayer film A5 is constituted by laminating, starting from the lower layer, the adhesive layer 40, the polyvinylidene chloride layer 12, the first heat-resistant resin substrate 11, and the adhesive layer 40.

The portion where the second multilayer film B5 is laminated becomes the air-impermeable portion. The second multilayer film B5 includes the vapor-deposited layer (air-impermeable layer) 22 obtained by vapor deposition on the second heat-resistant resin substrate 21. The portion where the first multilayer film A5 is laminated becomes the low air-permeability portion. The first multilayer film A5 includes the polyvinylidene chloride layer (low air-permeability layer) 12 laminated on the first heat-resistant resin substrate 11.

The area of the low air-permeability portion can be adjusted by changing the area where the first multilayer film A5 is laminated. In FIGS. 5A to 5D, the laminated sheet is formed by laminating the first multilayer film A5 in only the region of one side adjacent to the heat-sealed portion C5 in the region including the peripheral portion of the sealant layer 30. Both ends of one laminated sheet are stacked each other so as to be heat-sealed. According to the implementation illustrated in FIGS. 5A to 5C, the ratio of the area of the low air-permeability portion to the total internal area of the accommodating portion is 15%.

Sixth Embodiment

The sixth embodiment is a modified example of the fifth embodiment. The low air-permeability layer and the air-impermeable layer are provided on one substrate. The low air-permeability portion has the substrate and the low air-permeability layer. The air-impermeable portion has the substrate and the air-impermeable layer. Those that have been described above can be used without any limitation as the substrate, the low air-permeability layer and the air-impermeable layer, the sealant layer, and the like.

Figure 6A:
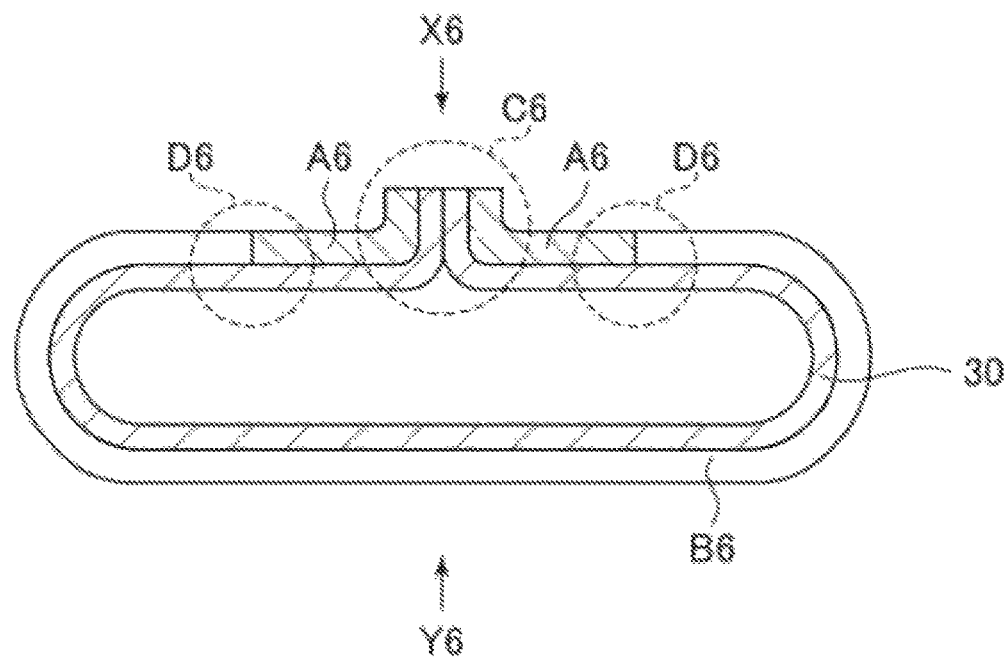
FIG. 6A is a cross-sectional view of an outer bag for disposable body warmer packaging in the Embodiment 6 of the present invention.
Figure 6B:
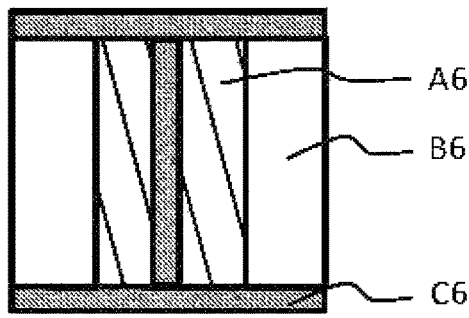
FIG. 6B is a plan view of the outer bag for disposable body warmer packaging in the Embodiment 6 of the present invention, where (a) is a plan view where the outer bag is viewed in the direction of an arrow X6 in FIG. 6A and (b) is a plan view where the outer bag is viewed in the direction of an arrow Y6 in FIG. 6A.
Figure 6B:
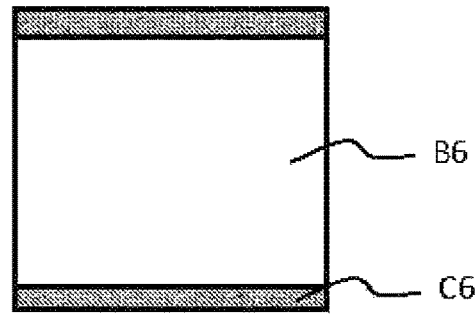
Figure 6C:
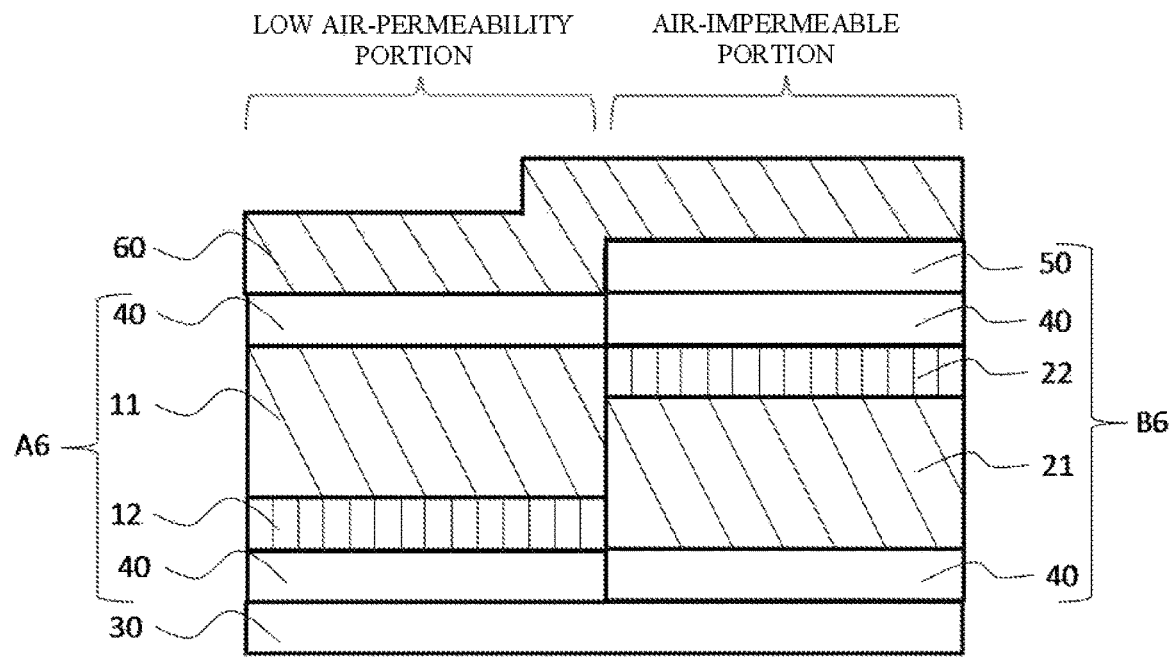
FIG. 6C is an explanatory view illustrating a layered structure of a cross section of a connected portion (D6 in the right side of FIG. 6A) of the outer bag for disposable body warmer packaging in the Embodiment 6 of the present invention.

The features of the outer bag for disposable body warmer packaging according to the sixth embodiment will be described with reference to FIGS. 6A to 6C. FIG. 6A is a cross-sectional view. FIG. 6B(a) is a plan view where the outer bag is viewed in the direction of an arrow X6 in FIG. 6A. FIG. 6B(b) is a plan view where the outer bag is viewed in the direction of an arrow Y6 in FIG. 6A. FIG. 6C is a cross-sectional view illustrating the laminated state in the connected portion indicated by D6 in the right section of FIG. 6A. The cross-sectional view of the laminated state in the connected portion indicated by D6 in the left section of FIG. 6A has its low air-permeability portion and air-impermeable portion in a horizontally inverted manner with reference to those in the cross-sectional view illustrating the laminated state in the connected portion D6 in the right section of FIG. 6C.

In the sixth embodiment, according to the outer bag for disposable body warmer packaging of the present invention, the laminated sheet is obtained by respectively joining the two first multilayer film A6 and the second multilayer film B6, on one sealant layer 30 by the two connected portions D6. The laminated sheet is wound so that the sealant layer 30 in on the inner surface' side of the outer bag. Both ends of the laminated sheet are stacked each other. The peripheral portion thereof is three-side pillow-sealed, and thus the bag can be formed. The space in the bag becomes the accommodating portion of the disposable body warmer. One of both ends of the laminated sheet includes the first multilayer films A5, and three-side pillow-sealing is conducted between these first multilayer films A5.

In FIG. 6A, the heat-sealed portion is indicated by C6.

In FIG. 6C, with regard to the connected portion D6, when viewed from the lower layer's side in FIG. 6C, the first multilayer film A6 and the second multilayer film B6 are adjacently laminated on the common sealant layer 30. Common additional resin layer 60 is laminated on the first multilayer film A6 and the second multilayer film B6, and thus the laminated sheet is constituted. The first multilayer film A6 is constituted by laminating, starting from the lower layer, the adhesive layer 40, the polyvinylidene chloride layer 12, the first heat-resistant resin substrate 11, and the adhesive layer 40. The second multilayer film B6 is constituted by laminating, starting from the lower layer, the adhesive layer 40, the second heat-resistant resin substrate 21, the vapor-deposited layer 22, the adhesive layer 40, and the printing ink layer 50.

The portion where the second multilayer film B6 is laminated becomes the air-impermeable portion. The second multilayer film B6 includes the vapor-deposited layer (air-impermeable layer) 22 obtained by vapor deposition on the second heat-resistant resin substrate 21. The portion where the first multilayer film A6 is laminated becomes the low air-permeability portion. The first multilayer film A6 includes the polyvinylidene chloride layer (low air-permeability layer) 12 laminated on the first heat-resistant resin substrate 11.

The area of the low air-permeability portion can be adjusted by changing the area where the first multilayer film A6 is laminated. In FIG. 6A to 6C, a laminated sheet is formed by laminating the first multilayer film A6 in the regions of both sides adjacent to the heat-sealed portion C6 in the region including the peripheral portion of the sealant layer 30. Both ends of one laminated sheet are stacked each other so as to be heat-sealed. According to the implementation illustrated in FIGS. 6A to 6C, the ratio of the area of the low air-permeability portion to the total internal area of the accommodating portion is 15%.

Seventh Embodiment

In the seventh embodiment, the low air-permeability layer and the air-impermeable layer are provided on one substrate. The above-described low air-permeability portion has the substrate and the low air-permeability layer. The air-impermeable portion has the substrate and the air-impermeable layer. Those that have been described above can be used without any limitation as the substrate, the low air-permeability layer and the air-impermeable layer, the sealant layer, and the others or the like.

Figure 7A:
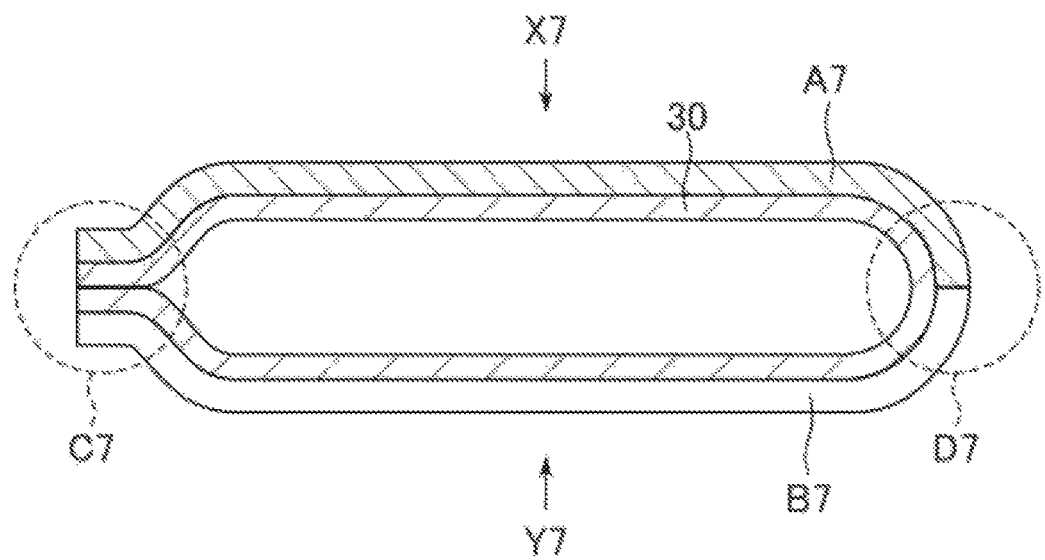
FIG. 7A is a cross-sectional view of an outer bag for disposable body warmer packaging in Embodiment 7 of the present invention.
Figure 7B:
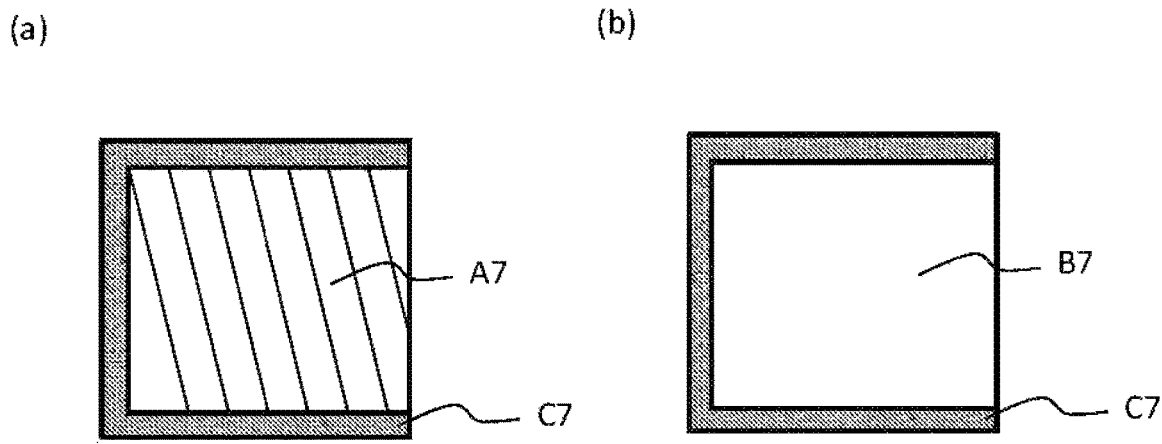
FIG. 7B is a plan view of the outer bag for disposable body warmer packaging in the Embodiment 7 of the present invention, where (a) is a plan view where the outer bag is viewed in the direction of an arrow X7 in FIG. 7A and (b) is a plan view where the outer bag is viewed in the direction of an arrow Y7 in FIG. 7A.
Figure 7C:
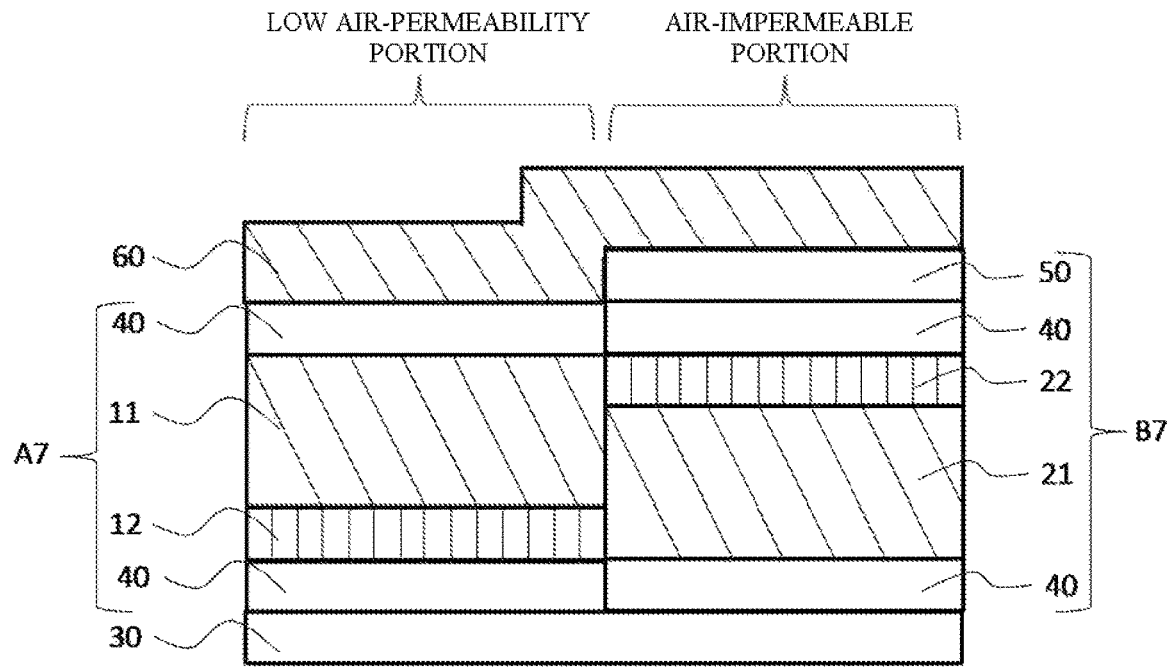
FIG. 7C is an explanatory view illustrating the layered structure of a cross section of a connected portion (D7 in FIG. 7A) of the outer bag for disposable body warmer packaging in the Embodiment 7 of the present invention.
Figure 7D:
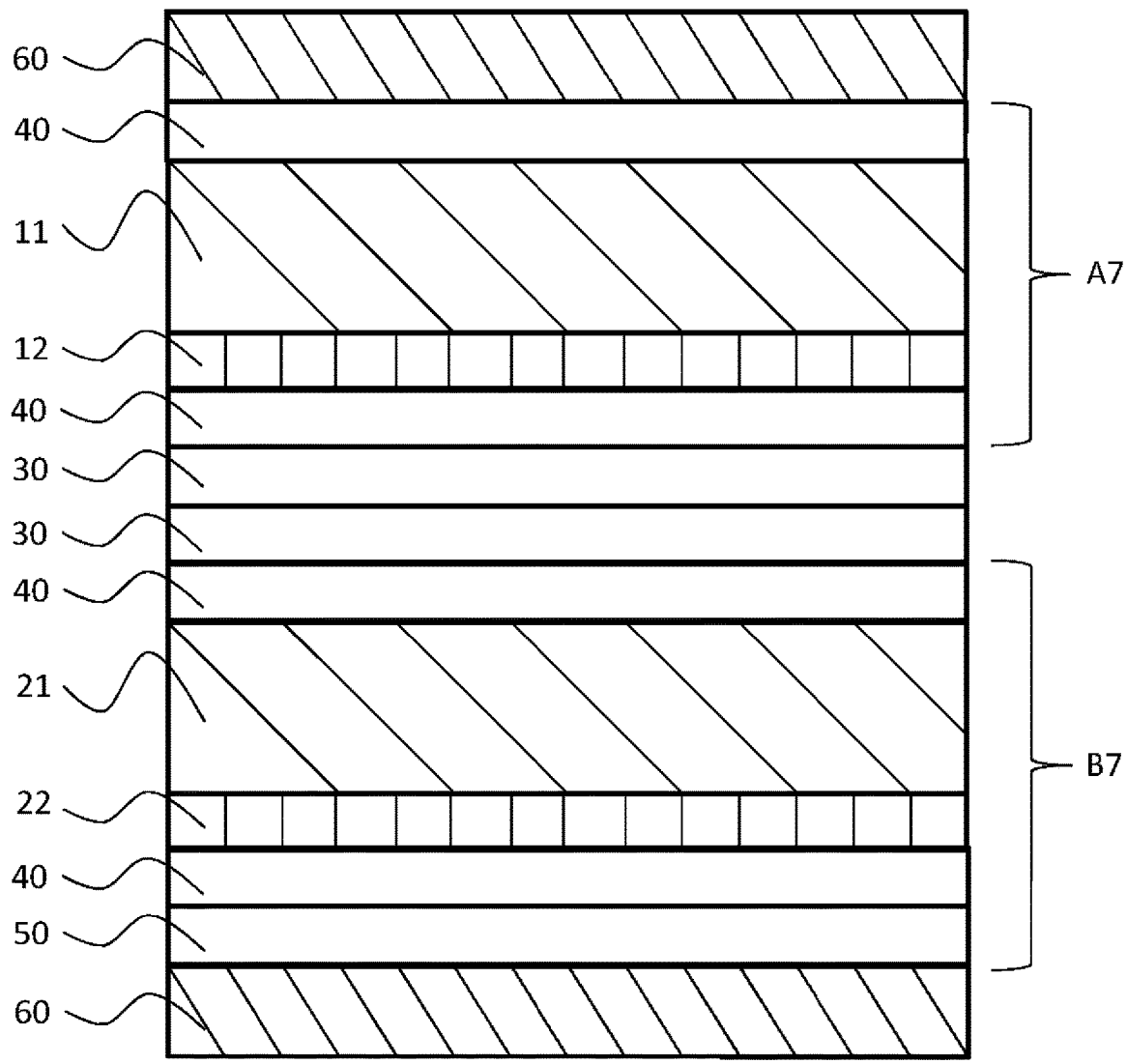
FIG. 7D is an explanatory view illustrating the layered structure of a cross section of a heat-sealed portion (C7 in FIG. 7A) of the outer bag for disposable body warmer packaging in the Embodiment 7 of the present invention.

The features of the outer bag for disposable body warmer packaging according to the seventh embodiment will be described with reference to FIGS. 7A to 7D. FIG. 7A is a cross-sectional view. FIG. 7B(a) is a plan view where the outer bag is viewed in the direction of an arrow X7 in FIG. 7A. FIG. 7B(b) is a plan view where the outer bag is viewed in the direction of an arrow Y7 in FIG. 7A. FIG. 7C is a cross-sectional view illustrating the laminated state in the connected portion indicated by D7 in FIG. 7A. FIG. 7D is a cross-sectional view illustrating the laminated state in the heat-sealed portion indicated by C7 in FIG. 7A.

In the seventh embodiment, according to the outer bag for disposable body warmer packaging of the present invention, the first multilayer film A7 and the second multilayer film B7 are joined on one sealant layer 30 by the connected portion D7. The three peripheral portions thereof are three-side sealed, and thus the bag can be formed, where the space in the bag becomes the accommodating portion of the disposable body warmer. The heat-sealed portion C7 includes the first multilayer film A7 and the second multilayer film B7.

With regard to the connected portion D7, when viewed from the lower layer's side in FIG. 7C, the first multilayer film A7 and the second multilayer film B7 are adjacently laminated on the common sealant layer 30. Common additional resin layer 60 is laminated on the first multilayer film A7 and the second multilayer film B7, and thus the laminated sheet is constituted. The first multilayer film A7 is constituted by laminating, starting from the lower layer, the adhesive layer 40, the polyvinylidene chloride layer 12, the first heat-resistant resin substrate 11, and the adhesive layer 40. The second multilayer film B7 is constituted by laminating, starting from the lower layer, the adhesive layer 40, the second heat-resistant resin substrate 21, the vapor-deposited layer 22, the adhesive layer 40, and the printing ink layer 50.

The heat-sealed portion C7 is constituted by laminating, when viewed from the lower layer of FIG. 7D, the second multilayer film B7, two respective sealant layers 30, and the first multilayer film A7 on the additional resin layer 60. The second multilayer film B7 is constituted by laminating, starting from the lower layer, the printing ink layer 50, the adhesive layer 40, the vapor-deposited layer 22, the second heat-resistant resin substrate 21, and the adhesive layer 40. The first multilayer film A7 is constituted by laminating, starting from the lower layer, an adhesive layer 40, the polyvinylidene chloride layer 12, the first heat-resistant resin substrate 11, and an adhesive layer 40.

The portion where the second multilayer film B7 is laminated becomes the air-impermeable portion. The second multilayer film B7 includes vapor-deposited layer (air-impermeable layer) 22 obtained by vapor deposition on the second heat-resistant resin substrate 21. The portion where the first multilayer film A7 is laminated becomes the low air-permeability portion. The first multilayer film A7 includes the polyvinylidene chloride layer (low air-permeability layer) 12 laminated on the first heat-resistant resin substrate 11. In the seventh embodiment, the first multilayer film A7 and the second multilayer film B7 constitute the front side and the back side of the bag, respectively. Thus, the ratio of the area of the low air-permeability portion to the total internal area of the accommodating portion is 50%.

Eighth Embodiment

In the eighth embodiment, the low air-permeability portion has a first substrate and a low air-permeability layer laminated on the first substrate. The air-impermeable portion has a second substrate and an air-impermeable layer laminated on the second substrate. Those that have been described above can be used without any limitation as the first substrate, the second substrate, the low air-permeability layer and the air-impermeable layer, the sealant layer, and the like.

The features of the outer bag for disposable body warmer packaging according to the eighth embodiment will be described with reference to FIGS. 8A to 8C.

Figure 8A:
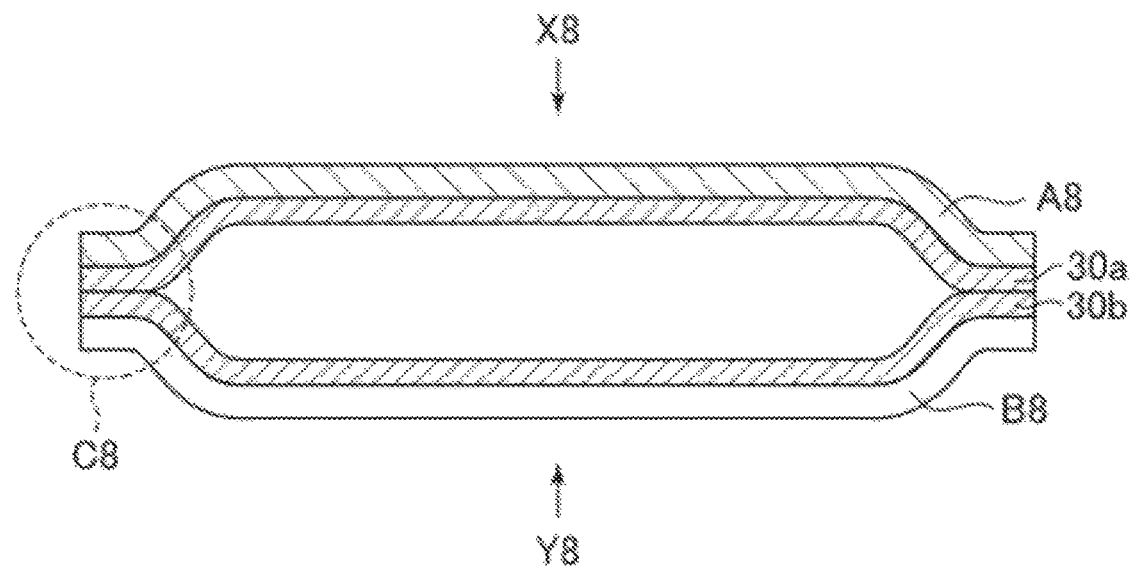
FIG. 8A is a cross-sectional view of an outer bag for disposable body warmer packaging in the Embodiment 8 of the present invention.
Figure 8B:
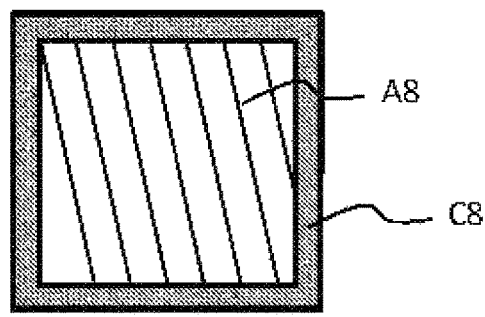
FIG. 8B is a plan view of the outer bag for disposable body warmer packaging in the Embodiment 8 of the present invention, where (a) is a plan view where the outer bag is viewed in the direction of an arrow X8 in FIG. 8A and (b) is a plan view where the outer bag is viewed in the direction of an arrow Y8 in FIG. 8A.
Figure 8B:
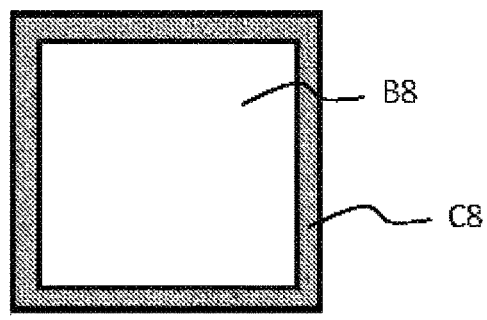

FIG. 8A is a cross-sectional view. FIG. 8B(a) is a plan view where the outer bag is viewed in the direction of an arrow X8 in FIG. 8A. FIG. 8B(b) is a plan view where the outer bag is viewed in the direction of an arrow Y8 in FIG. 8A. FIG. 8C is a cross-sectional view illustrating the laminated state in the heat-sealed portion indicated by C8 in FIG. 8A.

In the eighth embodiment, according to the outer bag for disposable body warmer packaging of the present invention, the first multilayer film A8 laminated on the first sealant layer 30a and the second multilayer film B8 laminated on the second sealant layer 30b are stacked each other. The peripheral portions thereof are four-side sealed, and thus the bag can be formed. The space in the bag becomes the accommodating portion of the disposable body warmer.

Figure 8C:
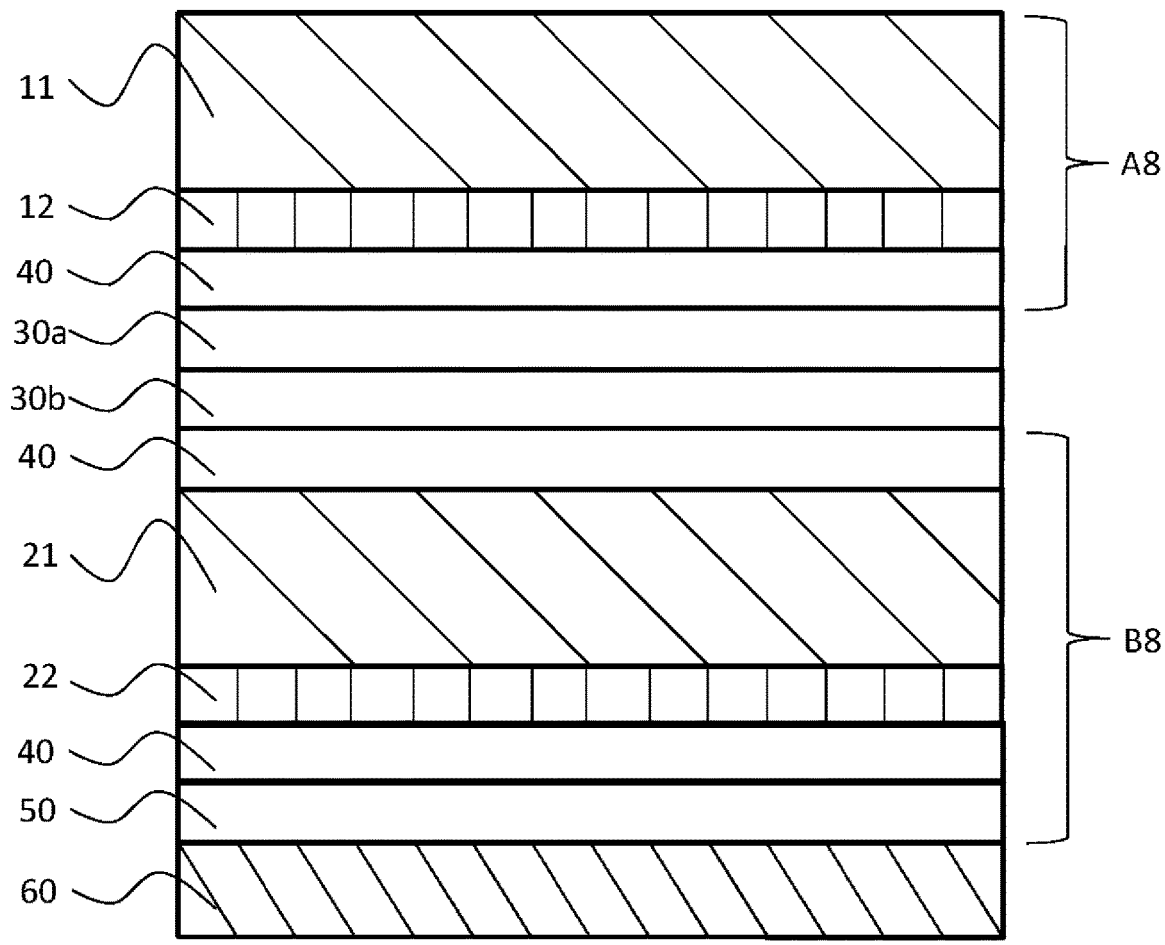
FIG. 8C is an explanatory view of the layered structure of a cross section of a heat-sealed portion (C8 in FIG. 8A) of the outer bag for disposable body warmer packaging in the Embodiment 8 of the present invention.

FIG. 8C illustrates the layered structure of the first multilayer film A8 and the second multilayer film B8 in the heat-sealed portion C5. In FIG. 8C, the first multilayer film A8 and the second multilayer film B8 are laminated in a state where the first sealant layer 30a and the second sealant layer 30b face each other. When viewed from the lower layer's side in FIG. 8C, the second multilayer film B8 is laminated on the additional resin layer 60, and the second sealant layer 30b, the first sealant layer 30a, and the first multilayer film A8 are laminated on the second multilayer film B8. The second multilayer film B8 is obtained by laminating, starting from the lower layer's side, the printing ink layer 50, the adhesive layer 40, the vapor-deposited layer 22, the second heat-resistant resin substrate 21, and the adhesive layer 40. The first multilayer film A8 is obtained by laminating, starting from the lower layer's side, the adhesive layer 40, the polyvinylidene chloride layer 12, and the first heat-resistant resin substrate 11. The portion where the second multilayer film B8 is laminated becomes the air-impermeable portion. The second multilayer film B8 includes the vapor-deposited layer (air-impermeable layer) 22 obtained by vapor deposition on the second heat-resistant resin substrate 21. The portion where the first multilayer film A8 is laminated becomes the low air-permeability portion. The first multilayer film A8 includes the polyvinylidene chloride layer (low air-permeability layer) 12 laminated on the first heat-resistant resin substrate 1. In the eighth embodiment, the first multilayer film A8 and the second multilayer film B8 constitute the front side and the back side of the bag respectively. Thus, the ratio of the area of the low air-permeability portion to the total internal area of the accommodating portion is 50%.

Ninth Embodiment

The ninth embodiment is a modified example of the eighth embodiment. In the same manner as in the eighth embodiment, the low air-permeability portion has a first substrate and a low air-permeability layer laminated on the first substrate. The air-impermeable portion has a second substrate and an air-impermeable layer laminated on the second substrate. Those that have been described above can be used without any limitation as the substrate, the low air-permeability layer and the air-impermeable layer, the sealant layer, and the like.

The features of the outer bag for disposable body warmer packaging according to the ninth embodiment will be described with reference to FIGS. 9A to 9C.

Figure 9A:
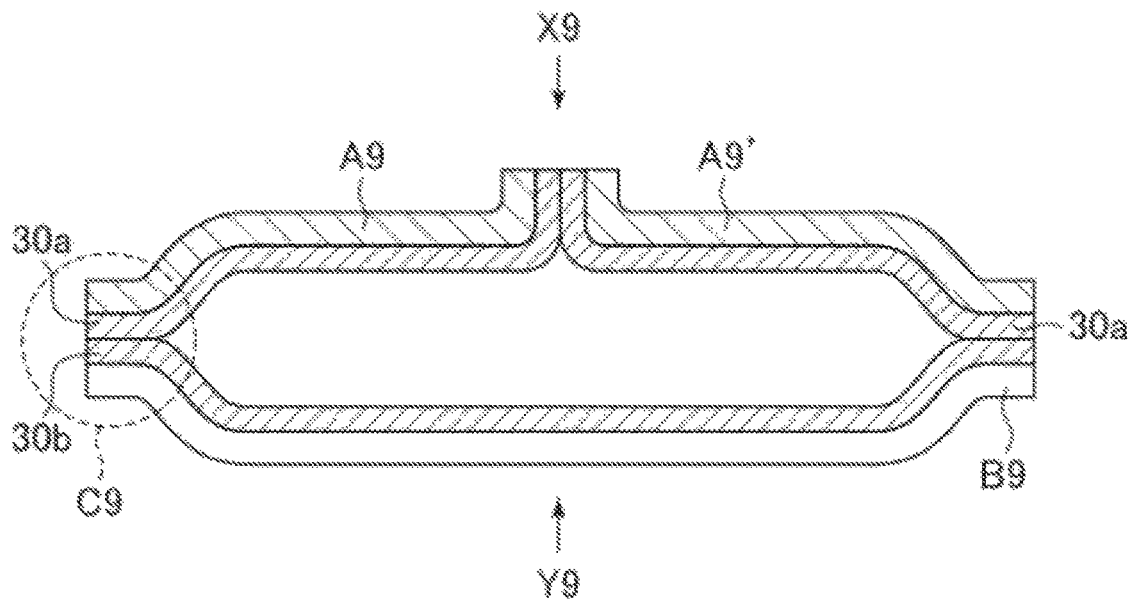
FIG. 9A is a cross-sectional view of an outer bag for disposable body warmer packaging in the Embodiment 9 of the present invention.
Figure 9B:
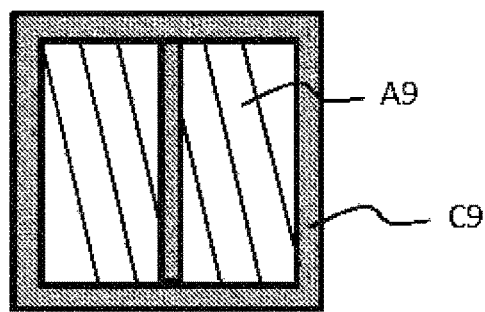
FIG. 9B is a plan view of the outer bag for disposable body warmer packaging in the Embodiment 9 of the present invention, where (a) is a plan view where the outer bag is viewed in the direction of an arrow X9 in FIG. 9A and (b) is a plan view where the outer bag is viewed in the direction of an arrow Y9 in FIG. 9A.
Figure 9B:
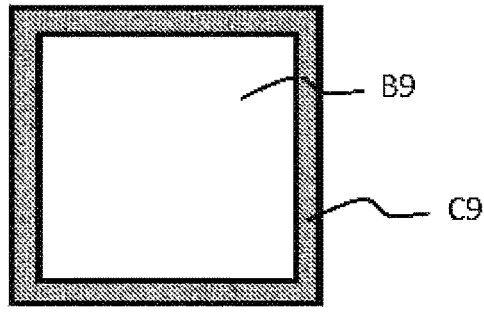

FIG. 9A is a cross-sectional view. FIG. 9B(a) is a plan view where the outer bag is viewed in the direction of an arrow X9 in FIG. 9A. FIG. 9B(b) is a plan view where the outer bag is viewed in the direction of an arrow Y9 in FIG. 9A. FIG. 9C is a cross-sectional view illustrating the laminated state in the heat-sealed portion indicated by C9 in FIG. 9A.

In the ninth embodiment, according to the outer bag for disposable body warmer packaging of the present invention, one end of the first multilayer film A9 laminated on the first sealant layer 30a and the one end of the first multilayer film A9' laminated on the first sealant layer 30a are partly stacked each other to be heat-sealed. Thereby the laminated sheet is formed such that the low air-permeability portion of the first multilayer film A9 and the low air-permeability portion of the first multilayer film A9' are adjacently positioned on the surface of the bag (the side viewed in the direction indicated by the arrow X9 in FIG. 9A). The first multilayer film A9 and the first multilayer film A9' may be multilayer films of the same or different configurations. The laminated sheet on the back side of the bag (the side viewed in the direction of an arrow Y9 in FIG. 9A) is formed by the second multilayer film B9 laminated on the second sealant layer 30b. In addition, the laminated sheets on the front side and the back side of the bag are stacked each other. The peripheral portion thereof is four-side sealed, and thus a bag can be formed. The space in the bag becomes the accommodating portion of the disposable body warmer.

Figure 9C:
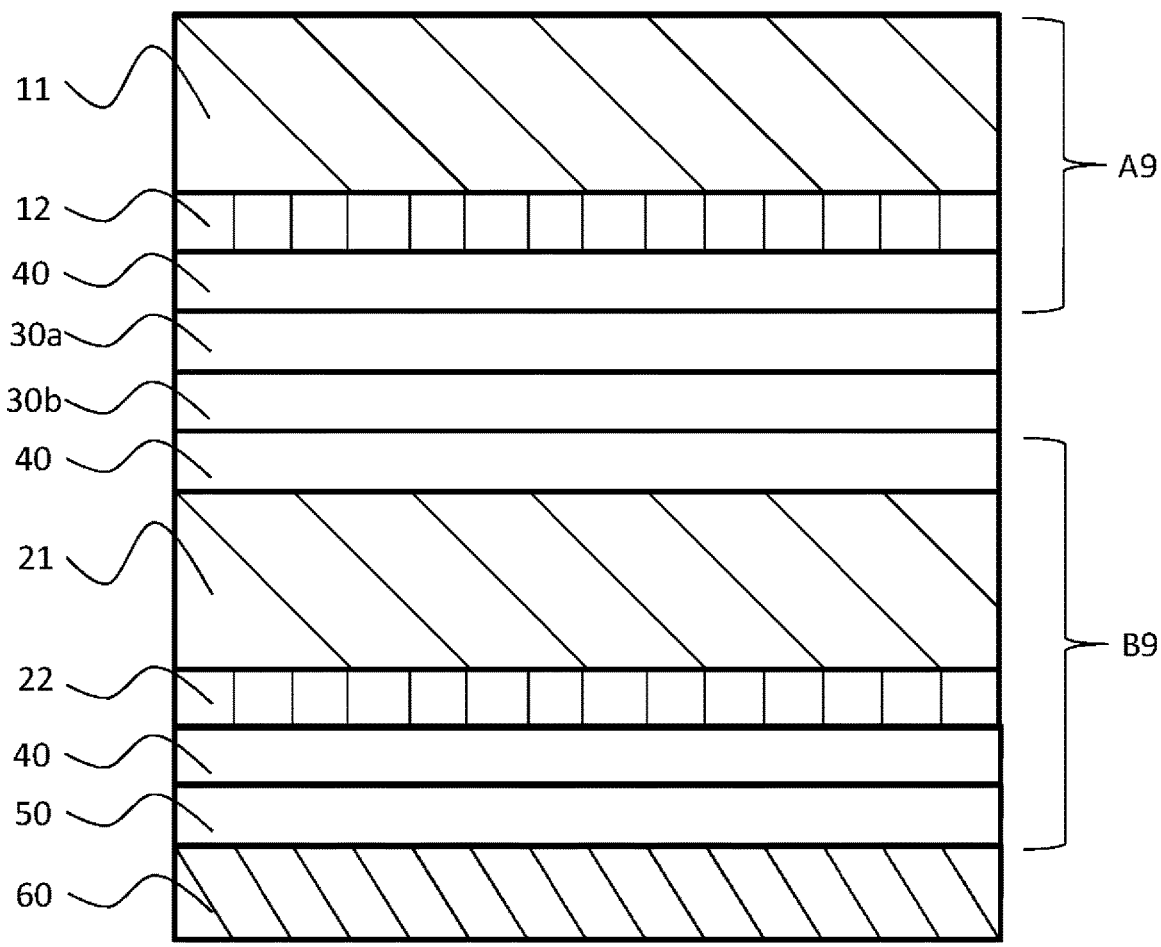
FIG. 9C is an explanatory view of the layered structure of a cross section of heat-sealed portion (C9 in FIG. 9A) of the outer bag for disposable body warmer packaging in the Embodiment 9 of the present invention.

FIG. 9C illustrates a layered structure of the first multilayer film A9 and the second multilayer film B9 in the heat-sealed portion C9. In FIG. 9C, they have the same layered structure as that of FIG. 8C of the eighth embodiment. The portion where the second multilayer film B9 is laminated becomes the air-impermeable portion. The second multilayer film B9 includes the vapor-deposited layer (air-impermeable layer) 22 obtained by vapor deposition on the ninth heat-resistant resin substrate 21. The portion where the first multilayer film A9 is laminated becomes the low air-permeability portion. The first multilayer film A9 includes the polyvinylidene chloride layer (low air-permeability layer) 12 laminated on the first heat-resistant resin substrate 11. In the ninth embodiment, the front side of the bag is constituted with ratios of the areas where the first multilayer film A9 and the first multilayer film A9' each occupy 50% of it. The back side of the bag is constituted by the second multilayer film B9. Thus, the ratio of the area of the low air-permeability portion to the total internal area of the accommodating portion is 50%.

The lamination conditions of the individual layers constituting the first multilayer film and the second multilayer film in the outer bag for disposable body warmer packaging of the present invention are not limited to those of the implementations described in the first embodiment to the ninth embodiment. For example, an implementation has been illustrated where the first heat-resistant resin substrate 11, the polyvinylidene chloride layer 12, and the sealant layer 30 are laminated in this order. But the lamination may be in the order of the polyvinylidene chloride layer 12, the first heat-resistant resin substrate 11, and the sealant layer 30.

The position of the sealant layer 30 in the outer bag for disposable body warmer packaging is not particularly limited, and it suffices that it is provided on the inner surface of the outer bag. But it may be provided on the outer surface of the outer bag. By providing the sealant layer 30 on the outer side of the polyvinylidene chloride layer 12, it is made possible to prevent the polyvinylidene chloride layer 12 from being damaged due to external contact and the gas barrier property from being impaired.

Also, the number and the shapes of low air-permeability portions and the air-impermeable portions in the outer bag for disposable body warmer packaging are not particularly limited, and may be selected from the group consisting of one or more circles, one or more quadrangles, one or more rectangles, one or more triangles, and combinations thereof.

The outer bag for disposable body warmer packaging of the present invention illustrated in FIGS. 1A to 9C includes a low air-permeability portion having an oxygen permeability of 1.5 to 20 $cc/m^2 \cdot day \cdot atm$ measured at 20° C. and 90% RH and having a water vapor permeability of 0.05 to 10 $g/m^2 \cdot day$ measured at 40° C. and 90% RH; and an air-impermeable portion having an oxygen permeability of 1.3 $cc/m^2 \cdot day \cdot atm$ or lower measured at 20° C. and 90% RH and a water vapor permeability of 2.0 $g/m^2 \cdot day$ or lower measured at 40° C. and 90% RH. Thereby, intrusion of oxygen into the inside of the outer bag from the outside of the outer bag is blocked to some extent, and permeation of hydrogen from the inside of the outer bag to the outside of the outer bag is allowed. By virtue of this, oxidation of metals such as the iron powders in the exothermic composition accommodated in the inner bag of the disposable body warmer is effectively prevented until it is used, and swelling of the outer bag due to hydrogen generated while it is stored is effectively prevented. Further, by including the low air-permeability portion and the air-impermeable portion, water vapor barrier property that inhibits permeation of water vapors is made higher. By virtue of this, intrusion of water into the inside of the outer bag from the outside of the outer bag can be prevented, also, the water contained as a constituent in the exothermic composition of the disposable body warmer and having the effect of promoting oxidation of metal such as iron powders, is prevented from being released as water vapor from the inside of the outer bag to the outside of the outer bag.

Conventional publicly-known methods can be used as the method for manufacturing the multilayer film for the outer bag for disposable body warmer packaging and the outer bag for disposable body warmer packaging of the present invention.

For example, the first multilayer film A and the second multilayer film B can be produced by pressure bonding of the first heat-resistant resin substrate 11 having the polyvinylidene chloride layer 12 on its surface, the second heat-resistant resin substrate 21 having the vapor-deposited layer 22 on its surface, the adhesive layer 40, the printing ink layer 50, the additional resin layer 60, and the sealant layer 30, which are in a laminated state, by use of a roll or the like.

Next, the first multilayer film A and the second multilayer film B are stacked each other, the peripheral portion of the sealant layer 30 is heat-sealed, and thereby they are formed in the shape of a bag. Any mode usually used can be used as the mode of heat-sealing without any limitation, and, for example, any heat-sealing form such as lateral sealing, two-side sealing, three-side sealing, four-side sealing, envelope-seam sealing, butt-seam sealing (pillow sealing), pleat sealing, flat bottom sealing, square bottom sealing, and gusset sealing forms may be adopted. Any heat-sealing method usually used can be used as the heat-sealing method without any limitation, and for example, bar sealing, rotating roll sealing, belt sealing, impulse sealing, high-frequency sealing, and ultrasonic sealing may be adopted.

The width of the heat-sealed portion in the outer bag for disposable body warmer packaging of the present invention is preferably 1 to 30 mm, more preferably 3 to 20 mm, and most preferably 5 to 10 mm.

The outer bag for disposable body warmer packaging of the present invention has a width dimension of preferably 30 to 300 mm, more preferably 40 to 250 mm, and most preferably 50 to 200 mm; a length dimension of preferably 30 to 300 mm, more preferably 40 to 250 mm, and most preferably 50 to 200 mm; and a thickness of preferably 5 to 2000 μm, and more preferably 10 to 1500 μm.

The volume of the accommodating portion of the outer bag for disposable body warmer packaging of the present invention is preferably 1 to 5000 ml, more preferably 10 to 2000 ml, and most preferably 20 to 500 ml.

The disposable body warmer of the present invention is made by packaging airtightly an inner bag accommodating an exothermic composition, in the outer bag for disposable body warmer packaging.

The exothermic composition may be any exothermic composition usually used for the disposable body warmer and is not in particular limited. For example, an exothermic composition may be adopted which contains metal powder such as iron powder, a reaction aid such as sodium chloride, activated carbon, a water-retaining agent, water and the like. Specifically, for example, an exothermic composition can be formed from 100 parts by weight of metal powders, for example, iron powders such as reduced iron powders or cast iron powders, or aluminum powders, 3 to 10 parts by weight of a reaction aid such as sodium chloride, 20 to 40 parts by weight of activated carbon and a water-retaining agent, 30 to 90 parts by weight of water, and the like. Herein, for example, an alkali metal hydroxide and a weakly basic alkali metal salt such as sodium hydroxide, potassium hydroxide, sodium hydrogen carbonate and sodium tertiary phosphate can be added as a hydrogen generation inhibitor to the exothermic composition, and the amount thereof to be used can be a trace amount relative to the metal powders.

In addition, the inner bag accommodating the exothermic composition may be air-permeable to such an extent that a metal can generate heat in the presence of oxygen, and for example, a bag article where one surface is prepared by an air-permeable packaging material and the other surface is prepared by an air-impermeable packaging material, or a bag article where both surfaces are each prepared by an air-permeable packaging material can be used. As the air-permeable packaging material, for example, a woven fabric or a non-woven fabric, a porous sheet where a plastic film, sheet or the like is perforated, or a composite sheet thereof can be used. In addition, as the air-impermeable packaging material, films or sheets of, for example, a polyethylene-based resin, a polypropylene-based resin, an ethylene-propylene copolymer, an ethylene-vinyl acetate copolymer, an ionomer resin, an ethylene-ethyl acrylate copolymer, an ethylene-acrylic acid or methacrylic acid copolymer, a methylpentene polymer, a polybutene-based resin, a polyvinyl acetate-based resin, a poly(meth)acrylic-based resin, a polyacrylonitrile-based resin, a polystyrene-based resin, an acrylonitrile-styrene copolymer (AS-based resin), an acrylonitrile-butadiene-styrene copolymer (ABS-based resin), a polyester-based resin, a polyamide-based resin, a polycarbonate-based resin, a polyvinyl alcohol-based resin, a saponified product of an ethylene-vinyl acetate copolymer, a fluororesin, a diene-based resin, a polyacetal-based resin, a polyurethane-based resin, nitrocellulose, or other known resins can be used. Any commonly known method can be used as the method for producing the inner bag without any limitation, and for example, any of various heat-sealing methods described above with respect to production of the outer bag can be preferably used.

The inner bag in the disposable body warmer of the present invention has the width dimension of preferably 50 to 300 mm, more preferably 75 to 200 mm, and most preferably 100 to 170 mm, and the length dimension of preferably 50 to 300 mm, more preferably 75 to 200 mm, and most preferably 100 to 170 mm, and the thickness of preferably 5 to 2000 μm, and more preferably 10 to 1500 μm.

In the disposable body warmer of the present invention, the volume of the accommodating portion of the outer bag for disposable body warmer packaging per calorific value 1 kcal of the exothermic composition in the inner bag is preferably 0.03 to 150 ml, more preferably 0.3 to 80 ml, and most preferably 0.6 to 20 ml. In the disposable body warmer of the present invention, by defining the volume of the accommodating portion of the outer bag for disposable body warmer packaging per calorific value 1 kcal of the exothermic composition in the inner bag within the above-identified numerical ranges, it is made possible to achieve the effect that it is excellent in a gas barrier property that inhibits permeation of oxygen gas, water vapor and the like, which can allow swelling due to hydrogen gas generated during a storage period to be prevented.

EXAMPLES

The present invention will be described below further specifically with reference to examples and comparative examples.

Example 1

A laminated sheet which has the polyvinylidene chloride layer 12 laminated on the biaxially oriented polypropylene film 11 (which is referred to as "KOPP#30") was prepared. The thickness of the biaxially oriented polypropylene film 11 is 30 μm and the thickness of the polyvinylidene chloride layer 12 is 1 μm. An ether-based adhesive was applied on the side of the polyvinylidene chloride layer 12 of the laminated sheet and was dried so as to form the adhesive layer 40. The straight-chain low density polyethylene film 30 (thickness of 30 μm) was placed on the laminated sheet via the adhesive layer 40 so as to be integrated therewith. Thus, the laminated sheet which constitutes the low air-permeability portion (hereinafter referred to as "low air-permeability portion laminated sheet") was produced. The low air-permeability portion laminated sheet had the dimensions of a width of 120 mm and a length of 165 mm. The low air-permeability portion laminated sheet was obtained by laminating the first multilayer film A1 consisting of the adhesive layer 40/polyvinylidene chloride layer 12/biaxially oriented polypropylene film 11 when viewed from the lower layer's side of the low air-permeability portion laminated sheet, on the straight-chain low density polyethylene film 30.

In the meantime, the printing ink layer 50 was formed by printing a character, graphic, sign, pattern, and the like on one side of the biaxially oriented polypropylene film 60 (thickness of 20 μm) using gravure printing. Next, an ether-based adhesive was applied on the printing ink layer 50 and dried so as to form the adhesive layer 40. A laminated sheet having the aluminum vapor-deposited layer 22 laminated on the biaxially oriented polyethylene terephthalate film 21 (which is referred to as "VMPET#12," where the thickness is 12 μm and the thickness of the vapor-deposited layer 22 is equal to or less than about 600 angstroms) was placed on and integrated with the adhesive layer 40 such that the adhesive layer 40 and the aluminum vapor-deposited layer 22 are brought into contact with each other. Further, the adhesive layer 40 was formed on the side opposite to the aluminum vapor-deposited layer 22 of the laminated sheet having the aluminum vapor-deposited layer 22 laminated on the biaxially oriented polyethylene terephthalate film 21. Then, the straight-chain low density polyethylene film 30 (thickness of 30 μm) was placed on the adhesive layer 40 and integrated therewith. The second multilayer film B1 consisting of the adhesive layer 40/biaxially oriented polyethylene terephthalate film 21/aluminum vapor-deposited layer 22/adhesive layer 40/printing ink layer 50 was positioned between the straight-chain low density polyethylene film 30 and the biaxially oriented polypropylene film 60. Thereby, a laminated sheet which constitutes an air-impermeable portion having the dimensions of a width of 120 mm and a length of 165 mm (hereinafter referred to as "air-impermeable portion laminated sheet") was produced.

In the same manner, a laminated sheet was produced using an aluminum film (which is referred to as "AL#7," where the thickness is 7 μm) in place of the laminated sheet having the aluminum vapor-deposited layer 22 laminated on the biaxially oriented polyethylene terephthalate film 21.

The oxygen permeability (cc/(m$^2$·day·atm)) and the water vapor permeability were measured on the two types that have been obtained in this manner, i.e., the low air-permeability portion laminated sheet and the air-impermeable portion laminated sheet under the following conditions (1) and (2). The measurement results are shown in table 1.

(1) Measurement of Oxygen Permeability

The following measurement machine was used under the following measurement conditions to measure the oxygen permeability (cc/(m$^2$·day·atm)) under the following temperature and humidity conditions.

Temperature: 20° C.; humidity: 90% RH
Measurement machine: OX-TRAN 2/20 manufactured by Mocon Inc.; measurement method: continuous measurement 20 times every 30 minutes (2) Measurement of Water Vapor Permeability The following measurement machine was used under the following measurement conditions to measure the water vapor permeability (g/(m$^2$·day)) under the following temperature and humidity conditions.

Temperature: 40° C.; humidity: 90% RH
Measurement machine: OX-TRAN 2/20 manufactured by Mocon Inc.; measurement method: continuous measurement 20 times every 30 minutes

TABLE 1

| Film used | Resin component of substrate | Thickness of substrate (μm) | Oxygen permeability (cc/(m$^2$ · day · atm)) | Water vapor permeability (g/(m$^2$ · day)) |
|---|---|---|---|---|
| Low air-permeability portion |||||
| KOPP#30 | PP | 30 | 5.9 | 4.5 |
| Air-impermeable portion |||||
| VMPET#12 | PET | 12 | 0.9 | 0.7 |
| AL#7 | AL | 7 | 0.1 | 0.05 |

Example 2

The following (3) Evaluation of appearance after acceleration test and (4) Evaluation of exothermic performance (duration) after acceleration test were conducted on the laminated sheet of the sample produced in the Example 1. The evaluation results are shown in Table 4.

(3) Evaluation of Appearance after Acceleration Test

The laminated sheet of the sample produced in the Example 1 was positioned as illustrated in the Embodiment 1 (FIGS. 1A to 1C). The low air-permeability portion laminated sheet and the air-impermeable portion laminated sheet were stacked such that a low air-permeability portion was provided in at least a part of a region adjacent to the heat-sealed portion and the ratios of the areas of the low air-permeability portion and the air-impermeable portion to the total internal area of the accommodating portion of the outer bag for disposable body warmer packaging each become 50%. Then, its peripheral portion was three-side pillow-sealed to form a heat-sealed portion. Thereby, a three-sides pillow-sealed outer bag for disposable body warmer packaging was produced. The three-sides pillow-sealed outer bag had the dimensions of: a width of 120 mm; a length of 165 mm; and a thickness of 130 μm, and had an opening at an upper portion thereof.

In the same manner, the outer bags for disposable body warmer packaging were produced except that ratios of the areas of the low air-permeability portion and the air-impermeable portion to the total internal area of the accommodating portion of the outer bag for disposable body warmer packaging were changed as indicated in Table 4.

An exothermic composition including 22 g of iron powder, 6 g of activated carbon, 6 g of a water-retaining agent, and 10 g of water was prepared. The exothermic composition was then charged and packaged in an inner bag to produce a stick type disposable body warmer. The inner bag includes an air-permeable porous sheet made of a polyethylene film and an air-impermeable sheet made of a polyethylene film adhered to each other. The stick type disposable body warmer includes an individual package and had the dimensions of: a width of 95 mm; a length of 130 mm; and a thickness of 5 mm.

Next, the disposable body warmer including an individual package, produced as described above, was charged through the opening portion of the outer bag for disposable body warmer packaging produced as described above. Thereafter, the opening portion was heat-sealed to form an upper sealing portion. Thereby, a disposable body warmer product having the size of a width of 120 mm; a length of 165 mm; and a thickness of 5.2 mm was produced. The disposable body warmer obtained in this manner showed that the volume of the accommodating portion of the outer bag for disposable body warmer packaging per 1 kcal of calorific value of the exothermic composition within the inner bag was 2.62 ml.

Five of the disposable body warmer products thus obtained were placed on a stage. The height (mm) of the five disposable body warmer products stacked (hereinafter, referred to as "height H1 (mm)") was measured. Next, the five disposable body warmer products stacked were stored at a temperature of 50° C. for three months. The height (mm) of the five disposable body warmer products stacked was measured every week for a period of three months. The height after a lapse of three months was defined as "height H2 (mm)." If any outer bag of the disposable body warmer products was swollen and broken during the storage period, the maximum height before such breakage was defined as the "height H2 (mm)." The value "H2−H1 (mm)" was then calculated, and rated as the appearance after an acceleration test, according to the following criteria of Table 2.

TABLE 2

| | |
|---|---|
| −3 < H2 − H1 (mm) < 3: | No change |
| −5 < H2 − H1 (mm) ≤ −3: | Slightly depressurizing tendency |
| H2 − H1 (mm) ≤ −5: | Depressurizing tendency |
| 3 ≤ H2 − H1 (mm) < 5: | Slightly swelling tendency |
| 5 ≤ H2 − H1 (mm): | Swelling tendency |

(4) Evaluation of Exothermic Performance (Duration) after Acceleration Test

A disposable body warmer product was produced in the same manner as in "(3) Evaluation of appearance after acceleration test" above.

The outer bags for disposable body warmer often of the disposable body warmer products thus obtained were opened to take out respective disposable body warmers. The exothermic performance of each of the disposable body warmers was tested based on JIS S4100. The duration average was defined as the "exothermic performance (duration)·initial" (hereinafter, referred to as "duration T1").

On the other hand, the ten disposable body warmer products obtained above were stored at a temperature of 50° C. for three months. Thereafter, respective outer bags for disposable body warmer were opened to take out respective disposable body warmers. The exothermic performance of each of the disposable body warmers was tested based on JIS S4100. The duration average was defined as "exothermic performance (duration)·after acceleration test" (hereinafter, referred to as "duration T2").

The value of T2/T1×100(%) was then calculated, and rated as the exothermic performance (duration) after an acceleration test, according to the following criteria of Table 3.

TABLE 3

| | |
|---|---|
| 95 < T2/T1 × 100(%) ≤ 100: | ◎ (Excellent) |
| 90 < T2/T1 × 100(%) ≤ 95: | ○ (Favorable) |
| 80 < T2/T1 × 100(%) ≤ 90: | Δ (Usable) |
| T2/T1 × 100(%) ≤ 80: | X (Not suitable as product) |

The heat-sealed portion was broken due to swelling, and heat generation was terminated before product opening:
(Not suitable as product)

TABLE 4

| No. | Ratio of area of low air-permeability portion (%) | Ratio of area of air-impermeable portion (%) | H2 − H1 (mm) | Evaluation of appearance | Exothermic performance (duration) |
|---|---|---|---|---|---|
| 1 | 50*[1] | 50*[2] | 0 | No change | ◎ |
| 2 | 15*[1] | 85*[2] | 0 | No change | ◎ |
| 3 | 10*[1] | 90*[2] | 1 | No change | ◎ |
| 4 | 5*[1] | 95*[2] | 3 | No change | ◎ |
| 5 | 1*[1] | 99*[2] | 4 | Slightly swelling tendency | ◎ |

*[1]Film included in the low air-permeability portion: KOPP#30
*[2]Film included in the air-impermeable portion: VMPET#12

Comparative Examples 1 and 2

The outer bags for disposable body warmer packaging having low air-permeability portion 100% or air-impermeable portion 100% were produced using only one type of the laminated sheet of the sample produced in the Example 1 in the same manner as in the Example 2.

Comparative Examples 3 to 5

Figure 10:
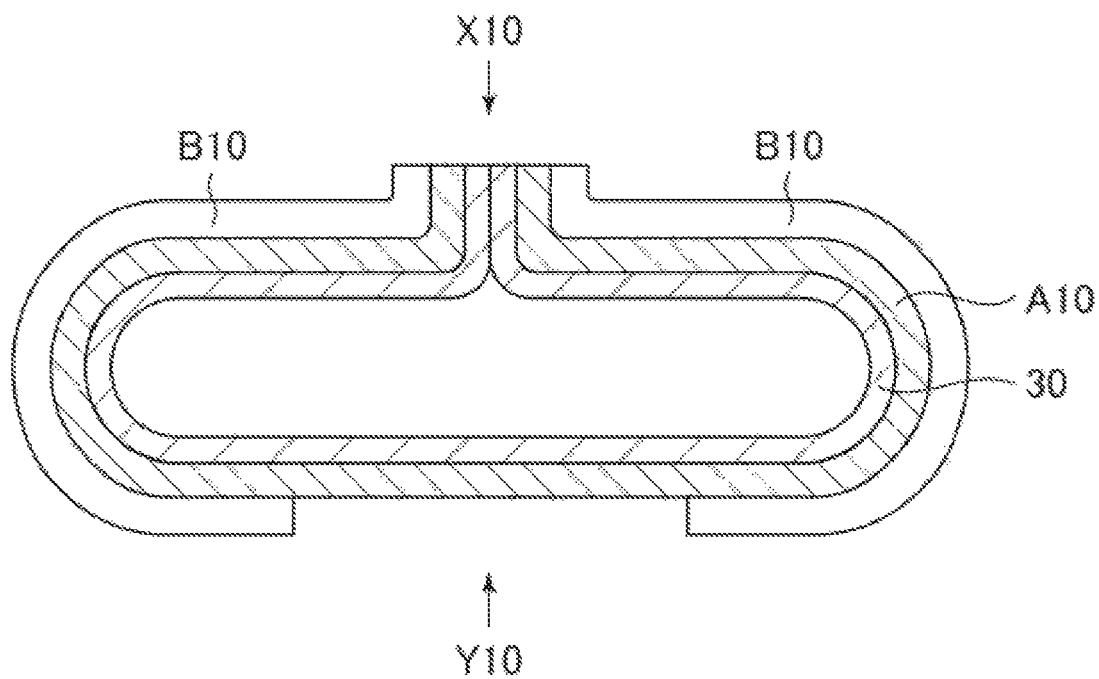
FIG. 10 is a cross-sectional view of an outer bag for disposable body warmer packaging in comparative examples 3 to 5.

The laminated sheet of the sample produced in the Example 1 was positioned as shown in FIG. 10. The low air-permeability portion laminated sheet and the air-impermeable portion laminated sheet were stacked such that no low air-permeability portion is provided in at least a portion of a region adjacent to the heat-sealed portion and the ratios of the areas of the low air-permeability portion and the air-impermeable portion to the total internal area of the accommodating portion of the outer bag for disposable body warmer packaging become 1% and 99%, respectively. Then, the peripheral portion thereof is three-side pillow-sealed to form a heat-sealed portion. Thus, a three-sides pillow-sealed outer bag for disposable body warmer packaging was produced. The three-sides pillow-sealed outer bag had the dimensions of: a width of 120 mm; a length of 165 mm; and a thickness 130 μm, and had an opening at an upper portion thereof. As illustrated in FIG. 10, the first multilayer film A10 is laminated on an entire surface of the sealant layer 30 but the second multilayer film B10 is not laminated on the entire surface thereof. The second multilayer film B10 is laminated on both end faces of the first multilayer film A10 but it does not exist in a region distant from the heat-sealed portion in FIG. 10.

In the same manner, outer bags for disposable body warmer packaging were produced except that ratios of the areas of the low air-permeability portion and the air-impermeable portion to the total internal area of the accommodating portion of the outer bag for disposable body warmer packaging are changed as shown in Table 5.

Comparative Example 6

In the same manner as in the Example 1 except that no polyvinylidene chloride layer is included, a printing ink layer and an adhesive layer were formed on one surface of a biaxially oriented polypropylene film (whose thickness is 20 μm; hereinafter referred to as "OPP#20"), and a straight-chain low density polyethylene film (having a thickness of 30 μm) was placed on this adhesive layer to be laminated on and integrated with it. A laminated sheet which is high air-permeability portion (hereinafter referred to as "high air-permeability portion laminated sheet") was produced. The high air-permeability portion laminated sheet was made of a straight-chain low density polyethylene film/adhesive layer/printing ink layer/biaxially oriented polypropylene film when viewed from the lower surface's side of the high air-permeability portion laminated sheet. Dimensions of the high air-permeability portion laminated sheet included a width of 120 mm and a length of 165 mm.

The oxygen permeability (cc/(m$^2$·day·atm)) and the water vapor permeability were measured on the high air-permeability portion laminated sheet thus obtained under the above-described conditions (1) and (2) in the same manner as in the Example 1. The measurement results are shown in Table 5.

Also, a three-sides pillow-sealed outer bag for disposable body warmer packaging having an opening on the upper portion thereof was produced in the same manner as in the Comparative Example 5 except for using high air-permeability portion laminated sheet in place of a low air-permeability portion laminated sheet.

In addition, (3) Evaluation of appearance after acceleration test and (4) Evaluation of exothermic performance (duration) after acceleration test were conducted on the outer bags for disposable body warmer packaging of the Comparative Examples 1 to 6 in the same manner as in the Example 2. The evaluation results are shown in Table 5.

to the outside. Therefore, they served sufficiently as a disposable body warmer even after storage for a long period.

On the other hand, in Comparative Examples 1 to 6, any change in appearance of a package product was observed before and after an acceleration test and each disposable body warmer product was not preferable in terms of appearance after storage for a long period. In addition, in Comparative Examples 2 and 6, each outer bag was slightly high in water vapor permeability, causing water vapor to easily penetrate. Thereby, moisture easily penetrates from the exterior into the interior of the outer bag, and also moisture included as an exothermic composition component of each disposable body warmer easily escapes to the outside. Therefore, they did not sufficiently generate heat as a disposable body warmer after storage for a long period. Furthermore, in Comparative Examples 1 and 3 to 5, swelling tendency was remarkably observed. Such swelling caused each heat-sealed portion to be broken. Each body warmer was brought into contact with outside air to terminate heat generation before each product was opened.

Also, a disposable body warmer was tested in the same manner as in the Example Nos. 1 to 5 except that a laminated sheet using the aluminum film described in Table 1 was used in place of the laminated sheet having a polyvinylidene chloride layer 12 laminated on a biaxially oriented polypropylene film 11 as the air-impermeable portion laminated sheet. The favorable results were similarly obtained as in the Example Nos. 1 to 5.

TABLE 5

| Comparative example | Film used | Oxygen permeability (cc/(m$^2$ · day · atm)) | Water vapor permeability (g/(m$^2$ · day)) | Area ratio (%) | H2 − H1 (mm) | Evaluation of appearance | Exothermic performance (duration) |
|---|---|---|---|---|---|---|---|
| 1 | VMPET#12 | 0.9 | 0.7 | 100% | 13 | — | — |
| 2 | KOPP#30 | 5.9 | 4.5 | 100% | −8 | Depressurizing tendency | X |
| 3 | KOPP#30 | 5.9 | 4.5 | 1% | 11 | — | — |
|   | VMPET#12 | 0.9 | 0.7 | 99% |  |  |  |
| 4 | KOPP#30 | 5.9 | 4.5 | 5% | 9 | — | — |
|   | VMPET#12 | 0.9 | 0.7 | 95% |  |  |  |
| 5 | KOPP#30 | 5.9 | 4.5 | 10% | 7 | — | — |
|   | VMPET#12 | 0.9 | 0.7 | 90% |  |  |  |
| 6 | OPP#20 | 1000 | 8.0 | 10% | −9 | Depressurizing tendency | X |
|   | VMPET#12 | 0.9 | 0.7 | 90% |  |  |  |

When the rating of the appearance in the above Tables 4 and 5 is "No change," "Slightly depressurizing tendency," or "Slightly swelling tendency," a disposable body warmer product is not changed in appearance even after storage for a long period and thus can be sold into a market as a product. On the other hand, when the rating of the appearance in Tables 4 and 5 is "Depressurizing tendency" or "Swelling tendency," a disposable body warmer product is not preferable because of being changed in appearance after storage for a long period.

As will be appreciated from the results in the above Tables 4 and 5, in Examples 1 to 4, no change in appearance of a package product was observed before and after an acceleration test and no degradation in exothermic function as a product was caused even after storage for a long period. In addition, in Examples 1 to 5, the outer bag for disposable body warmer packaging was low in water vapor permeability, allowing water vapor to not easily penetrate. Thereby, moisture did not easily penetrate from the exterior into the interior of the outer bag, and moisture included as a component of the disposable body warmer did not easily escape In addition, the exothermic composition was charged and packaged in an inner bag to produce a non-stick type disposable body warmer including an individual package. The inner bag comprises an air-permeable perforated sheet made of a polyethylene film and an air-impermeable sheet made of a polyethylene film adhered to each other. The disposable body warmer was tested in the same manner as in the Examples Nos. 1 to 5. The favorable results were similarly obtained as in the Examples Nos. 1 to 5.

REFERENCE SIGNS LIST

A1 to A9 multilayer film for outer bag for disposable body warmer packaging
11 heat-resistant resin substrate
12 polyvinylidene chloride layer
B1 to B9 multilayer film for outer bag for disposable body warmer packaging
21 heat-resistant resin substrate
22 vapor-deposited layer
30 sealant layer 40 adhesive layer
50 printing ink layer
60 additional resin layer

The invention claimed is:

1. An outer bag for disposable body warmer packaging having an accommodating portion accommodating a disposable body warmer accommodated in an air-permeable inner bag, the outer bag comprising:
a low air-permeability portion having an oxygen permeability of 1.5 to 20 cc/m$^2$·day·atm measured at 20° C. and 90% relative humidity and a water vapor permeability of 0.05 to 10 g/m$^2$·day measured at 40° C. and 90% relative humidity; and an air-impermeable portion having an oxygen permeability of 1.3 cc/m$^2$·day·atm or lower measured at 20° C. and 90% relative humidity and a water vapor permeability of 2.0 g/m$^2$·day or lower measured at 40° C. and 90% relative humidity,
wherein the outer bag for disposable body warmer packaging has at least one heat-sealed portion formed by heat-sealing one or more laminated sheets, and the low air-permeability portion is provided in at least a part of a region adjacent to the heat-sealed portion.

2. The outer bag for disposable body warmer packaging according to claim 1, wherein a ratio of area of the low air-permeability portion to a total internal area of the accommodating portion is 1 to 50%.

3. The outer bag for disposable body warmer packaging according to claim 1, wherein a low air-permeability layer and an air-impermeable layer are provided on one sealant layer, and the low air-permeability portion has the low air-permeability layer, and the air-impermeable portion has the low air-permeability layer and the air-impermeable layer.

4. The outer bag for disposable body warmer packaging according to claim 1, wherein a low air-permeability layer and an air-impermeable layer are provided on one sealant layer, and the low air-permeability portion has the low air-permeability layer, and the air-impermeable portion has the air-impermeable layer.

5. The outer bag for disposable body warmer packaging according to claim 1, wherein the low air-permeability portion has a first substrate and a low air-permeability layer laminated on the first substrate, and the air-impermeable portion has a second substrate and an air-impermeable layer laminated on the second substrate, and the first substrate and the second substrate are heat-sealed.

6. The outer bag for disposable body warmer packaging according to claim 3, wherein the low air-permeability layer comprises a homopolymer or copolymer of vinylidene chloride, and the air-impermeable layer comprises a metal or metal oxide.

7. A disposable body warmer packaged by the outer bag according to claim 1.

8. The outer bag for disposable body warmer packaging according to claim 4, wherein the low air-permeability layer comprises a homopolymer or copolymer of vinylidene chloride, and the air-impermeable layer comprises a metal or metal oxide.

9. The outer bag for disposable body warmer packaging according to claim 5, wherein the low air-permeability layer comprises a homopolymer or copolymer of vinylidene chloride, and the air-impermeable layer comprises a metal or metal oxide.

* * * * *